United States Patent
Futamura

(10) Patent No.: US 9,050,057 B1
(45) Date of Patent: Jun. 9, 2015

(54) MEDICAL IMAGE SYSTEM AND PROGRAM

(71) Applicant: KONICA MINOLTA, INC, Chiyoda-ku (JP)

(72) Inventor: Hitoshi Futamura, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 14/553,225

(22) Filed: Nov. 25, 2014

(30) Foreign Application Priority Data

Nov. 28, 2013 (JP) ................................. 2013-245717

(51) Int. Cl.
*G06K 9/00* (2006.01)
*A61B 6/00* (2006.01)
*A61B 8/08* (2006.01)

(52) U.S. Cl.
CPC ............... *A61B 6/5247* (2013.01); *A61B 6/502* (2013.01); *A61B 8/0825* (2013.01)

(58) Field of Classification Search
CPC ...... A61B 8/0825; A61B 8/406; A61B 8/463; A61B 8/483; A61B 8/14; A61B 2560/045; A61B 5/0002; A61B 5/0053; A61B 5/4312; A61B 5/48; A61B 6/032; G06T 7/0012
See application file for complete search history.

(56) References Cited

U.S. PATENT DOCUMENTS

| | | | | |
|---|---|---|---|---|
| 2005/0152592 A1* | 7/2005 | Kasai | ............................ | 382/132 |
| 2009/0264758 A1* | 10/2009 | Fujita et al. | ................... | 600/443 |
| 2010/0022881 A1* | 1/2010 | Fujita et al. | ................... | 600/445 |
| 2011/0208052 A1* | 8/2011 | Entrekin | ....................... | 600/437 |
| 2012/0243765 A1 | 9/2012 | Buelow et al. | | |

FOREIGN PATENT DOCUMENTS

JP    2013-514117    4/2013

* cited by examiner

*Primary Examiner* — Ali Bayat
(74) *Attorney, Agent, or Firm* — Cozen O'Connor

(57) ABSTRACT

A medical image system includes: a storage unit which stores a first medical image; a selection unit which selects a medical image to be associated with a second medical image; a designation unit which designates an abnormal shadow candidate; a reception unit which receives the second medical image newly created; a determination unit which determines whether or not the first medical image selected is an image suited for association, and the abnormal shadow candidate designated and the second medical image received satisfy a predetermined condition; an association unit which stores the second medical image in association with the abnormal shadow candidate; and a monitoring unit which monitors the association, outputs a warning, and stores the abnormal shadow candidate or the second medical image in association with information indicating there is no second medical image or abnormal shadow candidate to be associated, respectively.

8 Claims, 20 Drawing Sheets

| EXAMINATION ID | X-RAY IMAGE UID | ABNORMAL SHADOW CANDIDATE IDENTIFICATION INFORMATION | DESIGNATION FLAG | UID OF ULTRASONIC IMAGE TO BE ASSOCIATED |
|---|---|---|---|---|
| 0001 | X100001 | 1 | 0 | |
| | | 2 | 1 | U20001 U20003 |
| | | 3 | 2 | U20005 |
| | | 4 | 1 | NO ASSOCIATION |
| ... | ... | ... | ... | ... |

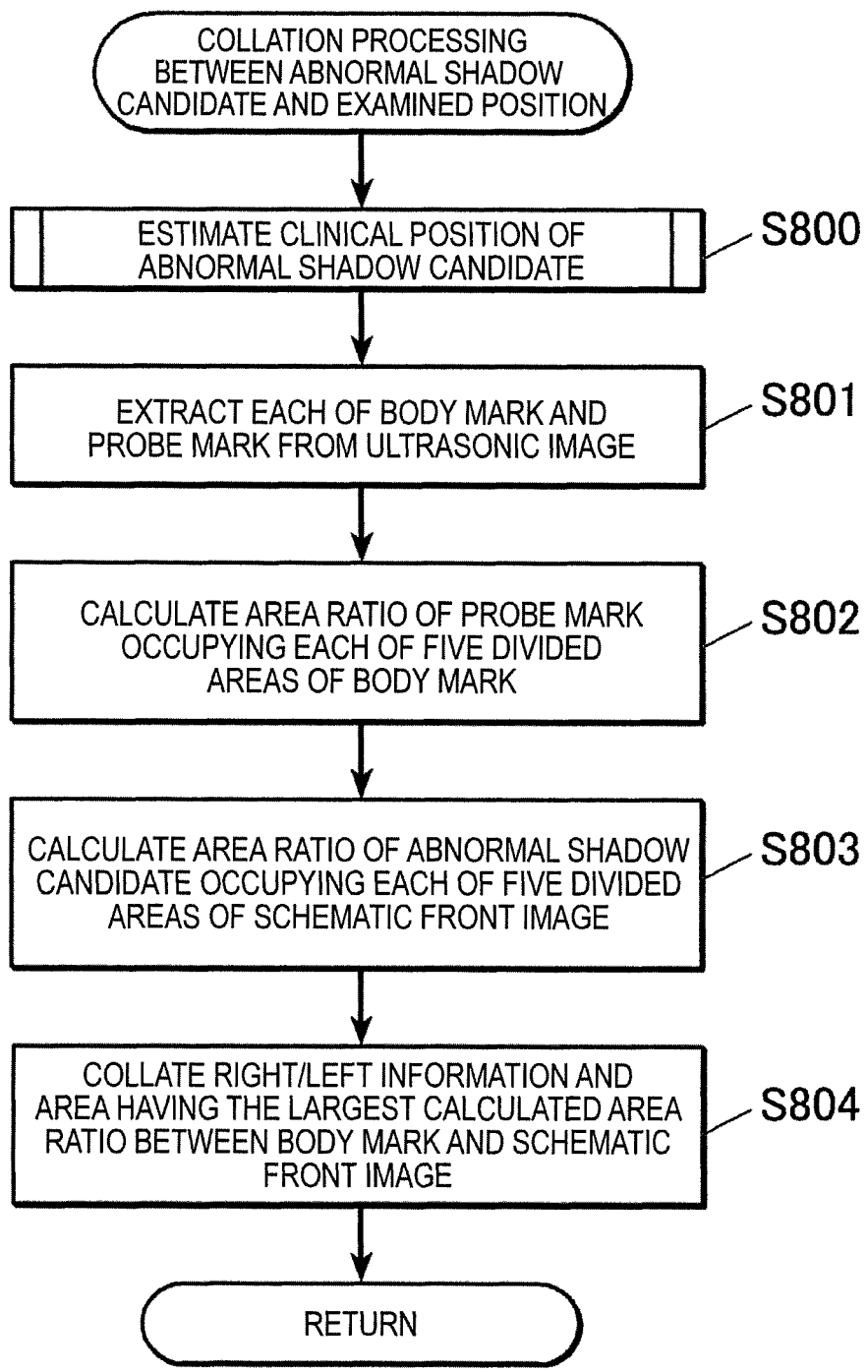

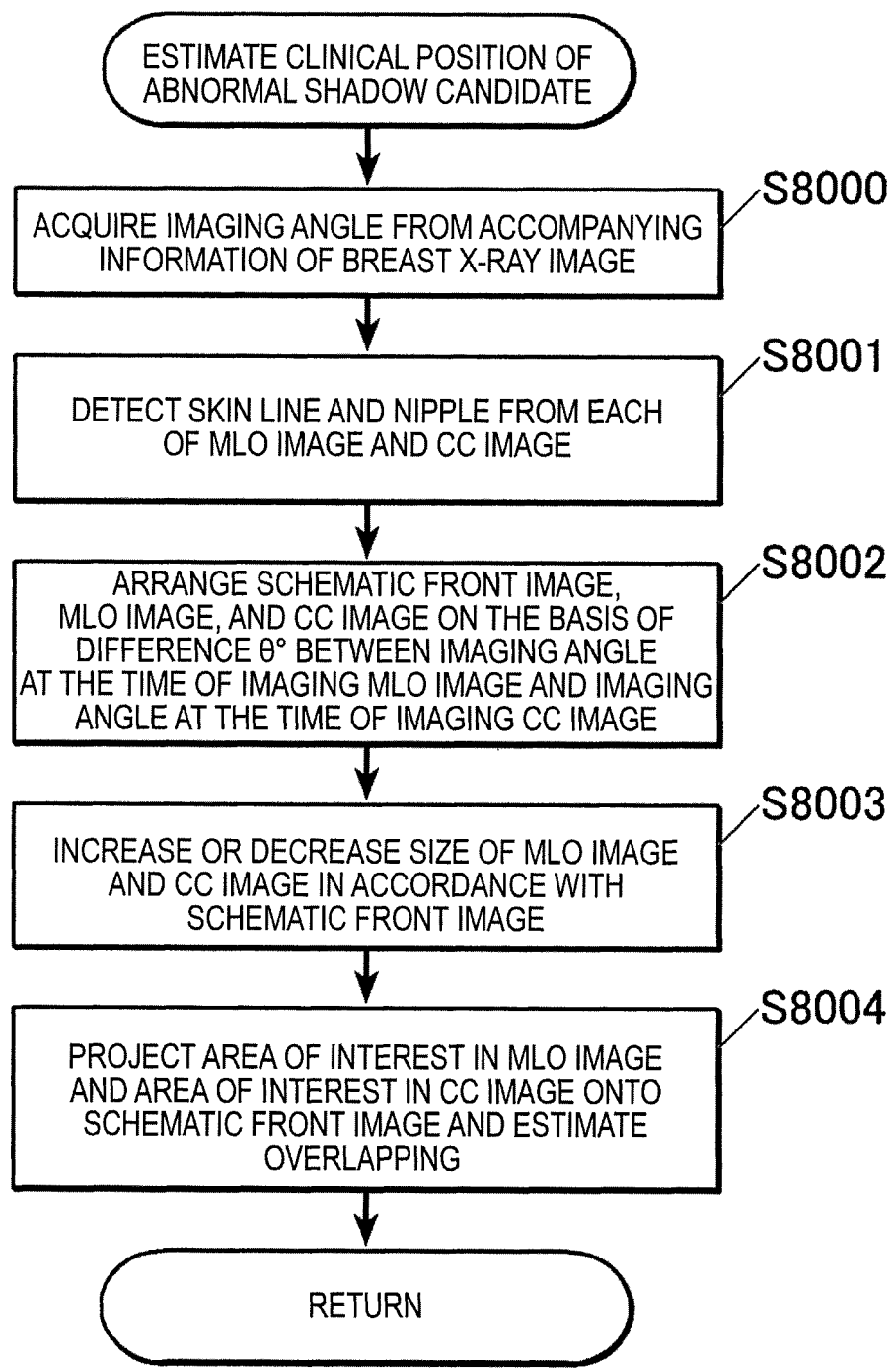

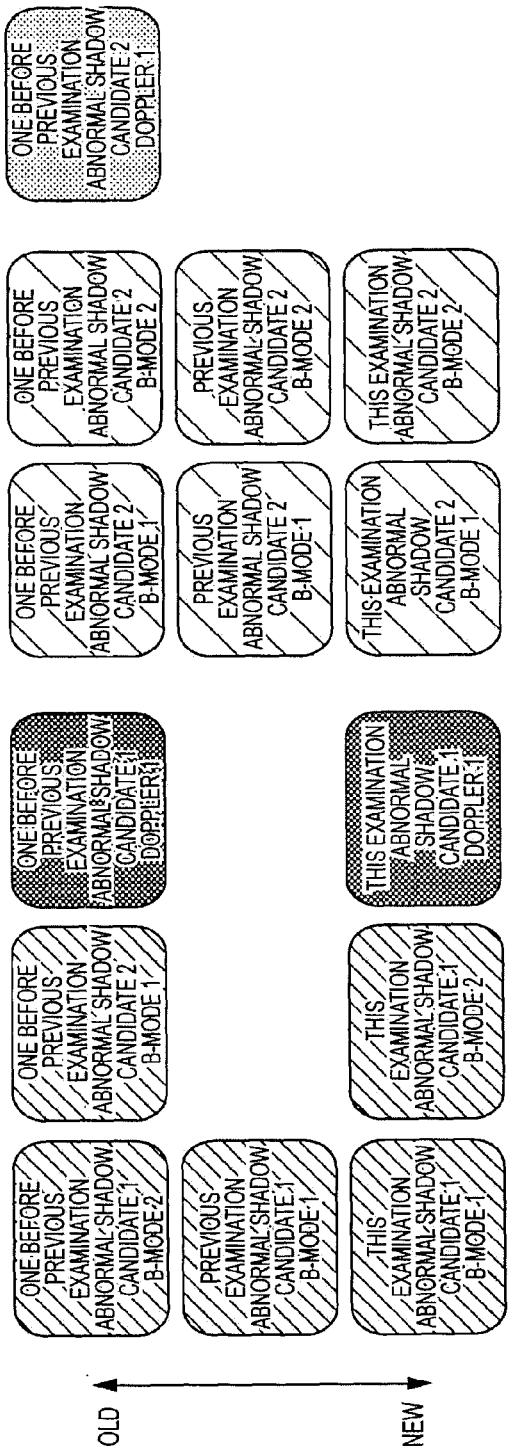
FIG. 15A
FIG. 15B
FIG. 15C

MEDICAL IMAGE SYSTEM AND PROGRAM

The entire disclosure of Japanese Patent Application No. 2013-245717 filed on Nov. 28, 2013 including description, claims, drawings, and abstract are incorporated herein by reference in its entirety.

BACKGROUND OF THE INVENTION

1. Field of the Invention

The present invention relates to a medical image system and a program.

2. Description of the Related Art

A mammography examination and an ultrasound examination have mainly been performed as a breast cancer examination in recent years. These two examinations can play complementary roles where one can expect to detect a lesion with higher accuracy by combining the two examinations to make a diagnosis.

Generally, in a combined examination, a radiology technician or the like first performs the mammography examination to obtain objective position information on an abnormal shadow candidate within a breast X-ray image that is obtained by radiography. A medical technologist or the like then performs the ultrasound examination while focusing on a location corresponding to an area of the abnormal shadow candidate within the breast X-ray image of abreast to generate an ultrasonic image of a mammary gland (hereinafter abbreviated as an ultrasonic image). Once both examinations are finished, a doctor interprets the breast X-ray image and the ultrasonic image to make a final diagnosis.

An image called a body mark is recorded in the ultrasound examination, the body mark being generated by superposing a probe mark which indicates a position (an examined position) scanned by an ultrasonic probe (probe) on the ultrasonic image obtained by the examination. It is however not easy for the doctor to perform the diagnosis by associating the abnormal shadow candidate in the breast X-ray image with the ultrasonic image while checking the body mark.

Now, for example, what is disclosed in JP 2013-514117 W is the generation of association with a selected object in a selected image when a new image is generated. According to JP, 2013-514117 W, an object (abnormal shadow candidate) in a medical image obtained in one examination can be associated with a medical image obtained in another examination.

However, some combinations of images may be associated with each other while other combinations of images are preferred not to be associated with each other. When the dates of examinations are too far apart from each other, for example, the images are preferably not associated with each other since the clinical condition has possibly undergone a change over-time between the images. The technology disclosed in JP 2013-514117 W however could not confirm such change, whereby the images that are preferably not associated with each other are associated with each other.

Moreover, it is not clear in the technology disclosed in JP 2013-514117 W whether an image is left unassociated or is determined by a technician to not have an image with which the image is associated, when the image is not associated. As a result, the doctor who makes the final diagnosis needs to take time to confirm this, causing a decrease in a diagnostic efficiency. This can also lead to re-examination, which undesirably increases a burden on both a patient and a hospital.

SUMMARY OF THE INVENTION

An object of the present invention is to prevent images that are not to be associated with each other from being associated with each other when an abnormal shadow candidate in a medical image imaged in one examination is associated with a medical image imaged in another examination, and to make it clear that there exists an abnormal shadow candidate or a medical image that is not associated when such candidate or image exists.

To achieve at least one of the above-mentioned objects, according to an aspect, a medical image system reflecting one aspect of the present invention comprises: a storage unit which stores a first medical image generated by a first imaging method in association with information on an abnormal shadow candidate in the first medical image; a selection unit which selects, from the first medical image stored in the storage unit, a medical image to be associated with a second medical image that is generated by a second imaging method different from the first imaging method; a designation unit which designates an abnormal shadow candidate from the first medical image selected; a reception unit which receives the second medical image newly created; a determination unit which determines whether or not the first medical image selected is an image suited for association and whether or not the abnormal shadow candidate designated and the second medical image received satisfy a predetermined condition to be associated; an association unit which stores in the storage unit the received second medical image in association with the abnormal shadow candidate designated when the first medical image selected is determined to be the image suited for association as well as the abnormal shadow candidate designated and the second medical image received are determined to satisfy the predetermined condition; and a monitoring unit which monitors the association performed by the association unit, outputs a warning when there exists an abnormal shadow candidate that is not associated with the second medical image or the second medical image that is not associated with any of the abnormal shadow candidate of the first medical image, and stores in the storage unit the abnormal shadow candidate, which is not associated with the second medical image, in association with information indicating that there is no second medical image to be associated as well as the second medical image, with which none of the abnormal shadow candidate of the first medical image is associated, in association with information indicating that there is no abnormal shadow candidate to be associated.

According to an aspect of the invention, the determination unit of the medical image system of Item. 1 preferably determines that the image is suited for association when the first medical image selected is the latest among the first medical images formed by imaging the same subject site of the same patient and is imaged within a predetermined period.

According to an aspect of the invention, the second medical image imaged by the medical image system of Item. 1 or 2 preferably records second clinical position information indicating an imaging position of the medical image when a subject site is viewed from the front, where the medical image system further comprises: a generation unit which generates first clinical position information indicating a position of the abnormal shadow candidate when the subject site of the first medical image is viewed from the front, on the basis of the first medical image being selected; an extraction unit which extracts the second clinical position information from the second medical image; and a collation unit which collates the first clinical position information with the second clinical position information, and the determination unit determines that the predetermined condition is satisfied when a result of the collation performed by the collation unit indicates that the first clinical position information matches the second clinical position information.

According to an aspect of the invention, the medical image system of any one of Items. 1 to 3 further preferably comprises a detection unit which detects the abnormal shadow candidate from the first medical image, and the storage unit stores the first medical image in association with information on the abnormal shadow candidate that is detected from the first medical image by the detection unit.

According to an aspect of the invention, the medical image system of any one of Items. 1 to 3 further preferably comprises an input unit which inputs an area corresponding to the abnormal shadow candidate in the first medical image, and the storage unit stores the first medical image in association with information on the abnormal shadow candidate that is input by the input unit.

According to an aspect of the invention, the medical image system of any one of Items. 1 to 5 further preferably comprises: a second designation unit which designates an abnormal shadow candidate from the first medical image selected; an abnormal shadow candidate extraction unit which reads from the storage unit the first medical image obtained by imaging the same subject site of the same patient as that in the first medical image including the abnormal shadow candidate designated by the second designation unit and extracts, from each first medical image being read, an abnormal shadow candidate that is located at about the same position as the abnormal shadow candidate designated by the second designation unit; and a display control unit which reads from the storage unit the second medical image stored in association with the abnormal shadow candidate extracted by the abnormal shadow candidate extraction unit, and arranges the second medical image being read in time series to be displayed on a display unit.

According to an aspect of the medical image system of any one of Items. 1 to 6, the first medical image is preferably a breast X-ray image, and the second medical image is preferably an ultrasonic image of a mammary gland.

To achieve at least one of the above-mentioned objects, according to an aspect, a non-transitory recording medium storing a computer readable program reflecting an aspect of the present invention causes a computer to function as: a selection unit which selects, from a storage unit which stores a first medical image generated by a first imaging method in association with information on an abnormal shadow candidate in the first medical image, a medical image to be associated with a second medical image that is generated by a second imaging method different from the first imaging method; a designation unit which designates an abnormal shadow candidate from the first medical image selected; a reception unit which receives the second medical image newly created; a determination unit which determines whether or not the first medical image selected is an image suited for association and whether or not the abnormal shadow candidate designated and the second medical image received satisfy a predetermined condition to be associated; an association unit which stores in the storage unit the second medical image in association with the abnormal shadow candidate designated when the first medical image selected is determined to be the image suited for association as well as the abnormal shadow candidate designated and the second medical image received are determined to satisfy the predetermined condition; and a monitoring unit which monitors the association performed by the association unit, outputs a warning when there exists an abnormal shadow candidate that is not associated with the second medical image or the second medical image that is not associated with any of the abnormal shadow candidate of the first medical image, and stores in the storage unit the abnormal shadow candidate, which is not associated with the second medical image, in association with information indicating that there is no second medical image to be associated as well as the second medical image, with which none of the abnormal shadow candidate of the first medical image is associated, in association with information indicating that there is no abnormal shadow candidate to be associated.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 5 is a diagram illustrating an example of a monitoring table;

FIG. 8 is a flowchart illustrating collation processing performed between an abnormal shadow candidate and an examined position in step S8 of FIG. 4A;

FIG. 9 is a flowchart illustrating processing executed in step S800 of FIG. 8;

FIG. 15A is a diagram illustrating an example of an ultrasonic image of one patient stored in an image DB, FIG. 15B is a diagram illustrating a series of images displayed when display order arrangement processing is performed by setting the type of the ultrasonic image to gray scale only from an image group in FIG. 15A, and FIG. 15C is a diagram illustrating a series of images displayed when the display order arrangement processing is performed by setting the type of the ultrasonic image to gray scale and color from the image group in FIG. 15A;

DESCRIPTION OF THE PREFERRED EMBODIMENTS

Hereinafter, an embodiment of the present invention will be described with reference to the drawings. However, the scope of the invention is not limited to the illustrated examples.

(Configuration of Medical Image System 100)

The configuration of an embodiment according to the present invention will be described first.

Figure 1:
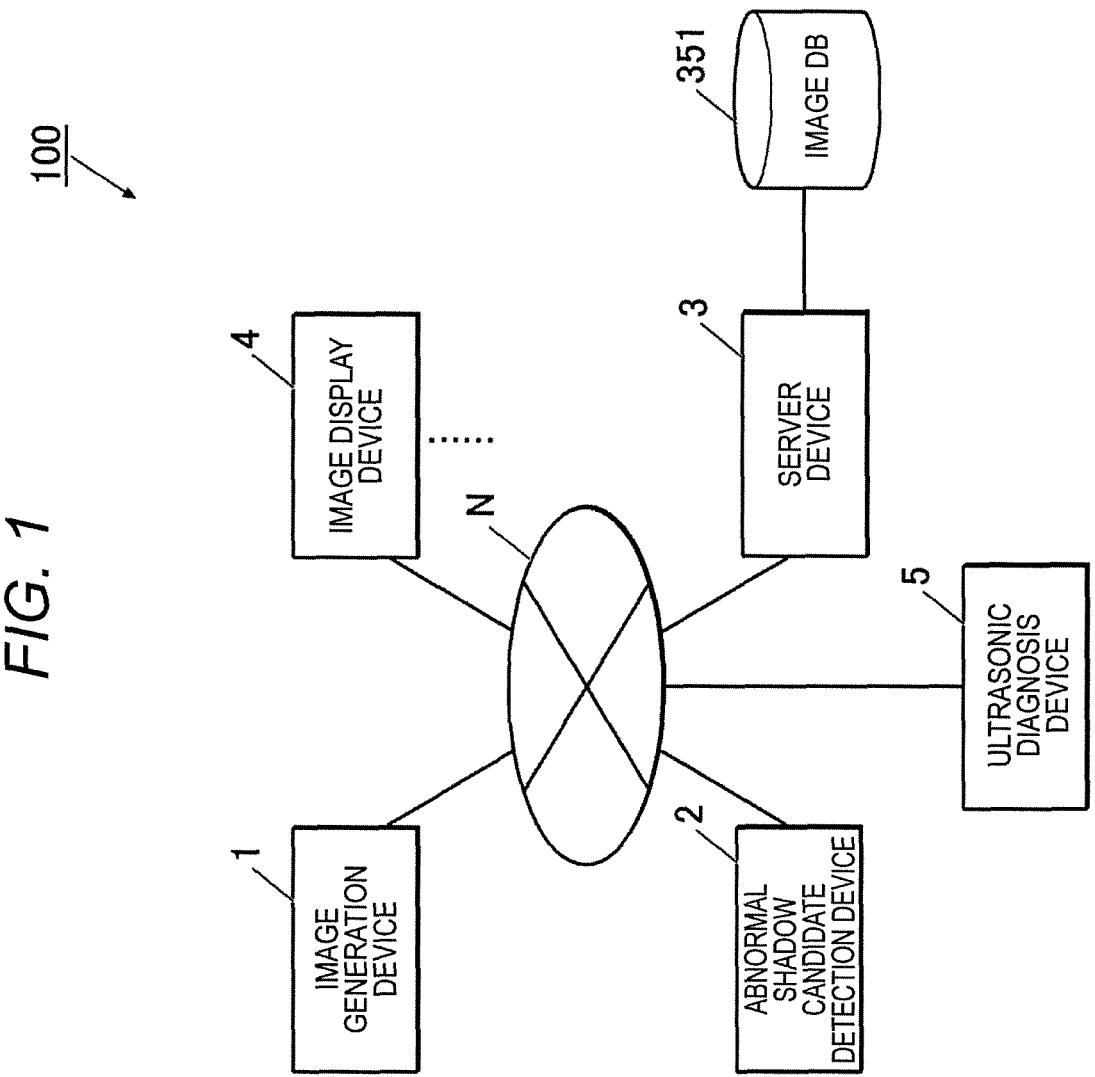
FIG. 1 is a diagram illustrating an example of an overall configuration of a medical image system according to an embodiment of the present invention.

FIG. 1 illustrates a system configuration of a medical image system 100 according to the present embodiment.

As illustrated in FIG. 1, the medical image system 100 includes an image generation device 1, an abnormal shadow candidate detection device 2, a server device 3, an image display device 4, and an ultrasonic diagnosis device 5. These devices 1 to 5 are connected through a communication network N such as a LAN (Local Area Network) established in a medical facility to be able to mutually transmit/receive data. A DICOM (Digital Imaging and Communication in Medicine) standard is applied to the communication network N. Note that the number of each device is not particularly limited.

The medical image system 100 is a system configured to cause the image generation device 1 to radiograph a subject site, store and manage an X-ray image obtained (a first medical image), and associate an abnormal shadow candidate in the X-ray image with an ultrasonic image (a second medical image) generated by the ultrasonic diagnosis device 5. While the medical image system 100 handles an X-ray image of various subject sites, there will be described an example in the present embodiment where mainly a breast is radiographed so that an abnormal shadow candidate in a breast X-ray image being obtained is associated with an ultrasonic image obtained in an ultrasound examination performed on the breast.

Each of the devices 1 to 5 will be described below.

The image generation device 1 is an X-ray imaging device which radiographs a subject site of a human body and generates digital data of the picked-up image (X-ray image), where a modality such as a CR (Computed Radiography) device and an FPD (Flat Panel Detector) can be used. In the present embodiment, the FPD device radiographing right and left breasts is used as the image generation device 1 to generate data of a breast X-ray image.

Note that the image generation device 1 is in conformity with the DICOM standard described above and can input from outside or automatically generate various information such as patient information and examination information accompanying each X-ray image generated. The patient information includes information such as patient identification information (such as a patient ID) which identifies a patient (subject) as well as a name, a sex, and a date of birth of the patient. The examination information includes information such as examination identification information (such as an examination ID) which identifies an examination, an examination date, an examination condition (an examined site, laterality (left and right), an imaging direction (such as a vertical direction (CC) and an oblique direction (MLO)), an imaging angle, and a modality type. Note that in the present embodiment, the same examination ID is assigned to a series of images (two right and left MLO images and CC images) obtained in a mammography examination of the same patient to manage the images. The image generation device 1 transmits, to the abnormal shadow candidate detection device 2 and the server device 3 through the communication network N, the generated X-ray image by adding thereto the patient information, the examination information and a UID (Unique ID) identifying an image as header information. When the device is not in conformity with the DICOM standard, a DICOM converter that is not shown can be used to input the accompanying information to the image generation device 1 as well.

The abnormal shadow candidate detection device (CAD) 2 serving as a detection unit is a computer which performs processing of detecting an abnormal shadow candidate by analyzing an X-ray image supplied from the image generation device 1. The abnormal shadow candidate detection device 2 includes a CPU (Central Processing Unit), a storage unit such as a RAM (Random Access Memory) and an HDD (Hard Disk Drive), and a communication unit such as a LAN card. The storage unit of the abnormal shadow candidate detection device 2 stores a detection program of a detection algorithm according to the type of an abnormal shadow, and the CPU of the abnormal shadow candidate detection device 2 executes abnormal shadow candidate detection processing in cooperation with the detection program stored in the storage unit to detect the abnormal shadow candidate from each X-ray image input through the communication unit. The abnormal shadow candidate detection device 2 detects an abnormal shadow candidate of a mass and a microcalcification cluster in the breast X-ray image, for example.

A known algorithm can be used as the detection algorithm of the abnormal shadow candidate. There can be used, as the algorithm for a mass shadow candidate in the breast X-ray image, a method using an iris filter disclosed in JP 10-91758 A and a method using a Laplacian filter (IEICE Transactions on Information and Systems (D-II), Vol. J76-D-II, no. 2, pp. 241-249, 1993), for example. Moreover, there can be used as the detection algorithm for a microcalcification cluster shadow candidate a method using a morphology filter (IEICE Transactions on Information and Systems (D-II), Vol. J71-D-II, no. 7, pp. 1170-1176, 1992), a Laplacian filter (IEICE Transactions on Information and Systems (D-II), Vol. J71-D-II, no. 10, pp. 1994-2001, 1998), and a triple ring filter, for example.

Once the abnormal shadow candidate is detected, the CPU of the abnormal shadow candidate detection device 2 generates abnormal shadow candidate information on the basis of the detected result of the abnormal shadow candidate. The abnormal shadow candidate information includes information identifying each abnormal shadow candidate detected, position information of an area corresponding to the abnormal shadow candidate, and information on the type of the abnormal shadow candidate (such as the mass and the microcalcification cluster), for example. The abnormal shadow candidate detection device 2 then adds the header information (at least the UID) of the X-ray image, from which the abnormal shadow candidate is detected, to the abnormal shadow candidate information generated and transmits it to the server device 3 through the communication unit.

The server device 3 configures a PACS (Picture Archiving and Communication System) together with the image display device 4 that is a client. The server device 3 stores, in a database (an image DB 351), the X-ray image generated in the image generation device 1 in association with the accompanying information, the abnormal shadow candidate information, and the ultrasonic image and manages the image and the information. Moreover, the server device 3 causes the image display device 4 to display a selection screen on which an X-ray image to be processed is selected and a viewer screen (not shown) displaying the X-ray image being selected, and executes various processings including association processing to be described below in accordance with operation information transmitted from the image display device 4.

Figure 2:
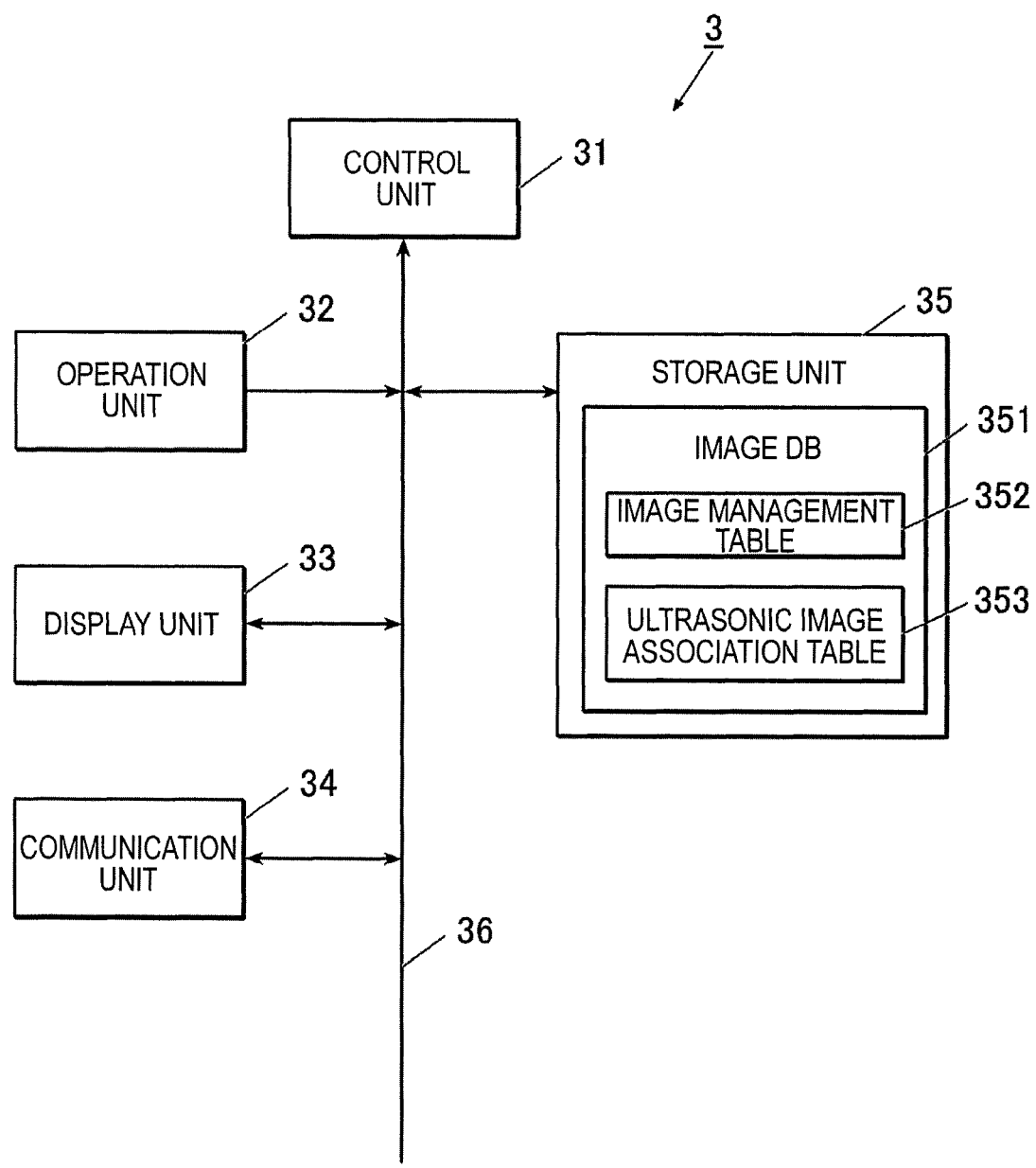
FIG. 2 is a block diagram illustrating a functional configuration of a server device illustrated in FIG. 1.

FIG. 2 illustrates an example of the functional configuration of the server device 3. As illustrated in FIG. 2, the server device 3 includes a control unit 31, an operation unit 32, a display unit 33, a communication unit 34, and a storage unit 35, where each unit is connected by a bus 36.

The control unit 31 includes a CPU (Central Processing Unit), a RAM (Random Access Memory), and the like. The CPU of the control unit 31 reads various programs such as a system program and a processing program stored in the storage unit 35, extracts the programs to the RAM, and executes various processings according to the extracted programs. The control unit 31 executes the association processing to be described below to function as a determination unit, an association unit, a monitoring unit, a generation unit, an extraction unit, a collation unit, an abnormal shadow candidate detection unit, and a display control unit.

The operation unit 32 includes a keyboard including a character input key, a number input key and various function keys and a pointing device such as a mouse, and outputs to the control unit 31 a depression signal of a key that is depressed on the keyboard and an operation signal by the mouse as an input signal.

The display unit 33 includes a monitor such as a CRT (Cathode Ray Tube) and an LCD (Liquid Crystal Display) to display various screens according to an instruction of a display signal being input from the control unit 31.

The communication unit 34 is formed of a LAN card and the like to transmit/receive data to/from an external device that is connected to the communication network N through a switching hub. The communication unit 34 functions as a reception unit.

The storage unit 35 includes an HDD (Hard Disk Drive) and a semiconductor non-volatile memory, for example. The storage unit 35 stores the various programs as described above. The storage unit 35 is further provided with the image DB 351.

The image DB 351 is a database storing an X-ray image and the like. The image DB 351 includes for example an image area which stores the medical image such as the X-ray image and the ultrasonic image, an image management table 352 which stores management information pertaining to each X-ray image stored in the image DB 351, and an ultrasonic image association table 353 which stores association information between an abnormal shadow candidate detected from each X-ray image and the ultrasonic image.

The image management table 352 stores the management information on each X-ray image as one record. The management information includes the UID, the patient information, the examination information, and file information (a file name of an X-ray image, a file name of abnormal shadow candidate information corresponding to the X-ray image, a file name of an ultrasonic image corresponding to the abnormal shadow candidate, a file storage location for each file, an updated date, and a file size).

For each examination (or in association with the examination ID), the ultrasonic image association table 353 stores identification information of each abnormal shadow candidate that is detected from each X-ray image obtained in the examination, in association with the UID of the ultrasonic image associated with the abnormal shadow candidate. Note that the identification information of the abnormal shadow candidate with which no ultrasonic image is associated is stored in association with a phrase "no association" indicating there is no ultrasonic image to be associated, instead of the UID of the ultrasonic image. Moreover, the ultrasonic image with which no abnormal shadow candidate is associated in the examination is stored in association with a phrase "no association" indicating that there is no abnormal shadow candidate to be associated, instead of the identification information of the abnormal shadow candidate.

Upon receiving the X-ray image from the image generation device 1 through the communication unit 34, the control unit 31 stores the received X-ray image in the image DB 351, creates management information on the basis of header information of the received X-ray image, and stores the management information in the image management table 352 of the image DB 351. Upon receiving the abnormal shadow candidate information from the abnormal shadow candidate detection device 2 through the communication unit 34, the control unit stores the received abnormal shadow candidate information in the image DB 351, retrieves from the image management table 352 a record with the UID matching the UID included in the abnormal shadow candidate information, and writes the file name and storage location of the abnormal shadow candidate information to the retrieved record. Upon receiving the ultrasonic image from the ultrasonic diagnosis device 5 through the communication unit 34, the control unit stores the received ultrasonic image in the image DB 351, retrieves from the image management table 352 a record of an X-ray image that is obtained in the examination and selected in advance as the record to be associated with the ultrasonic image, and writes the file name and storage location of the ultrasonic image to the retrieved record. Furthermore, the control unit 31 stores in the ultrasonic image association table 353 association information between the abnormal shadow candidate in the X-ray image and the ultrasonic image obtained by the association processing to be described below.

The image DB 351 thus retrievably stores the X-ray image in association with the abnormal, shadow candidate information of the abnormal shadow candidate detected from the X-ray image as well as the ultrasonic image corresponding to each abnormal shadow candidate.

The image display device 4 is configured to display the selection screen and the viewer screen transmitted from the server device 3, transmit operation information input through these screens to the server device 3, and display a processing result transmitted from the server device 3 and corresponding to the operation on the viewer screen. The image display device 4 functions as a selection unit, a designation unit, and a second designation unit.

Figure 3:
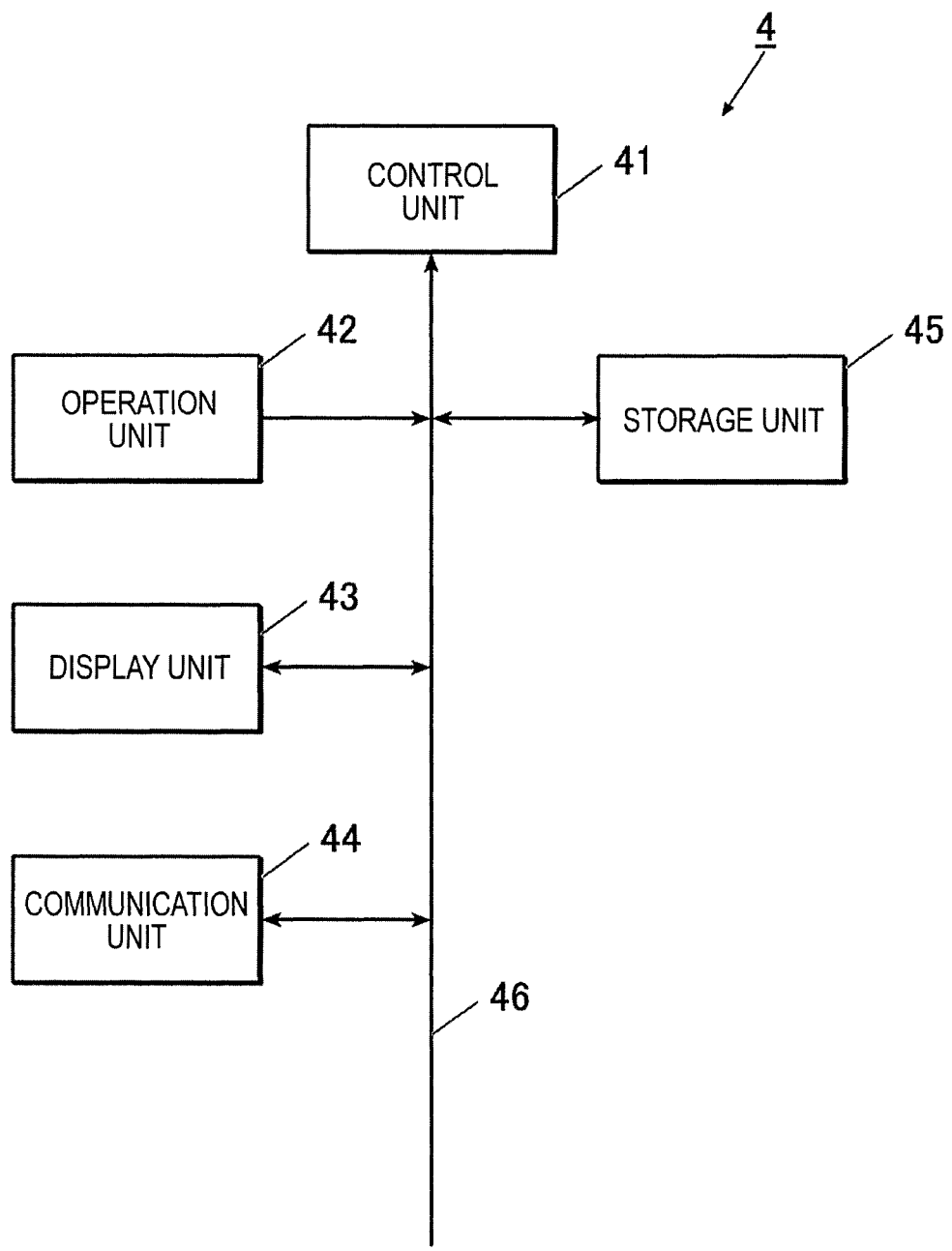
FIG. 3 is a block diagram illustrating a functional configuration of an image display device illustrated in FIG. 1.

FIG. 3 illustrates an example of the functional configuration of the image display device 4.

As illustrated in FIG. 3, the image display device 4 includes a control unit 41, an operation unit 42, a display unit 43, a communication unit 44, and a storage unit 45, where each unit is connected by a bus 46.

The control unit 41 is formed of a CPU, a RAM, and the like. The CPU of the control unit 41 reads various programs such as a system program and a processing program stored in the storage unit 45, extracts the programs to the RAM, and executes various processings according to the extracted programs.

The operation unit 42 includes a keyboard including a character input key, a number input key and various function keys and a pointing device such as a mouse, and outputs to the control unit 41 a depression signal of a key that is depressed on the keyboard and an operation signal by the mouse as an input signal.

The display unit 43 includes a monitor such as the CRT (Cathode Ray Tube) and the LCD (Liquid Crystal Display) to display various screens according to an instruction of a display signal being input from the control unit 41.

The communication unit 44 is formed of the LAN card and the like to transmit/receive data to/from an external device that is connected to the communication network N through a switching hub.

The storage unit 45 includes the HDD (Hard Disk Drive) and the semiconductor non-volatile memory, for example. The storage unit 45 stores the system program and the various programs (such as a program used to display various screens received from the server device 3 and a program used to transmit to the server device 3 through the communication unit 44 the operation information input from the operation unit 42) as described above.

The ultrasonic diagnosis device 5 transmits ultrasound (transmission ultrasound) to a subject site by using an ultrasonic probe as well as receives a reflected wave of the ultrasound (reflected ultrasound: echo) that is reflected within the subject site. The ultrasonic diagnosis device then converts the reflected wave being received into an electric signal and generates the ultrasonic image on the basis of the signal. The ultrasonic diagnosis device 5 further includes an operation unit which inputs a body mark indicating the position at which the ultrasonic probe is placed and a communication unit which communicates with the server device 3 connected to the communication network N, where the body mark input by the operation unit is recorded in the ultrasonic image being generated, and the UID identifying the image, the patient information, and the examination date are written in a header as the accompanying information and transmitted to the server device 3 through the communication unit. Note that the ultrasonic diagnosis device 5 in the present embodiment is intended for breast examination. Moreover, the UID is an ID specific to the ultrasonic image and not overlapping with the UID of the X-ray image.

(Operation of Medical Image System 100)

The operation of the medical image system 100 will now be described.

Figure 4A:
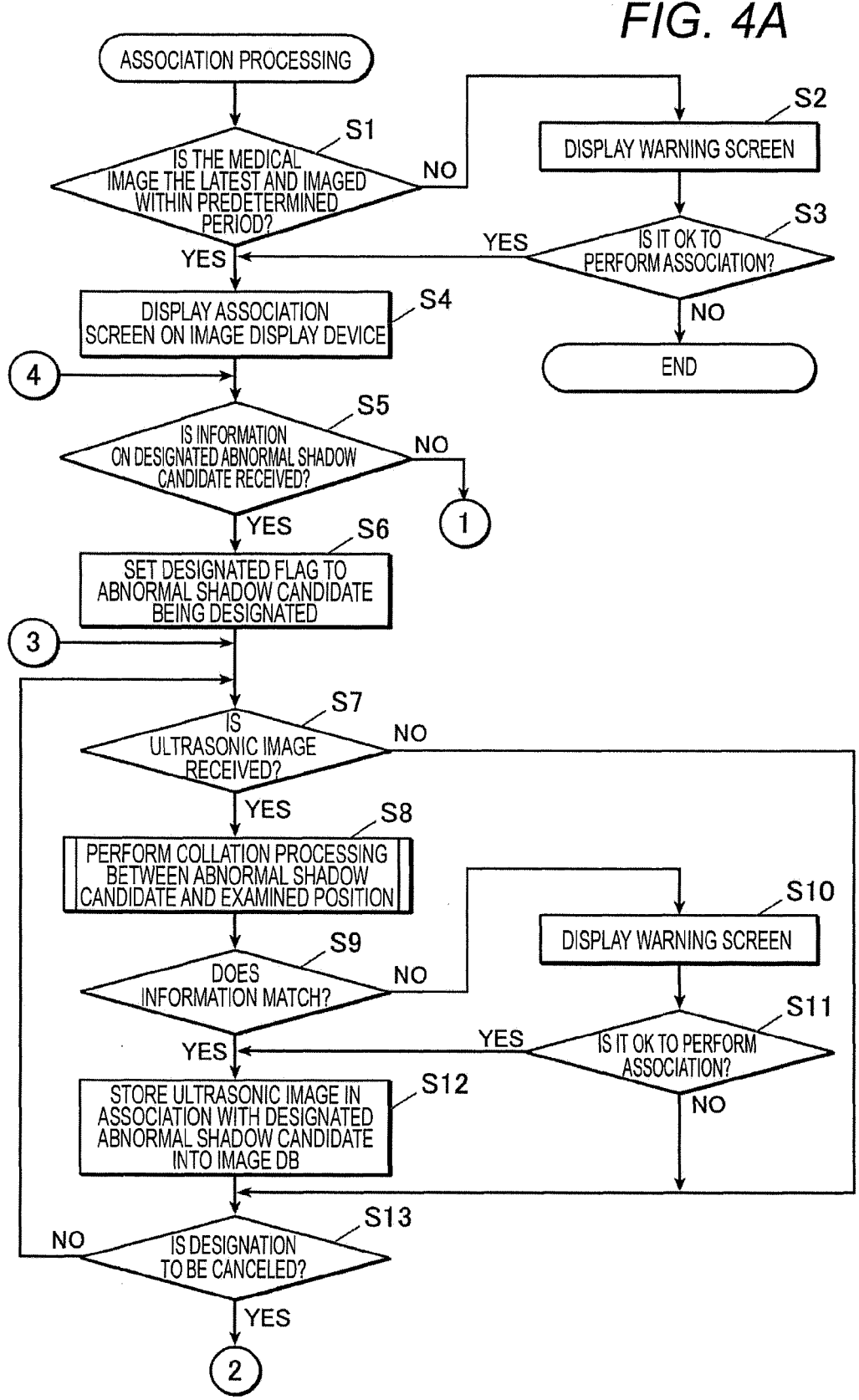
FIG. 4A is a flowchart illustrating association processing executed by a control unit illustrated in FIG. 2.
Figure 4B:
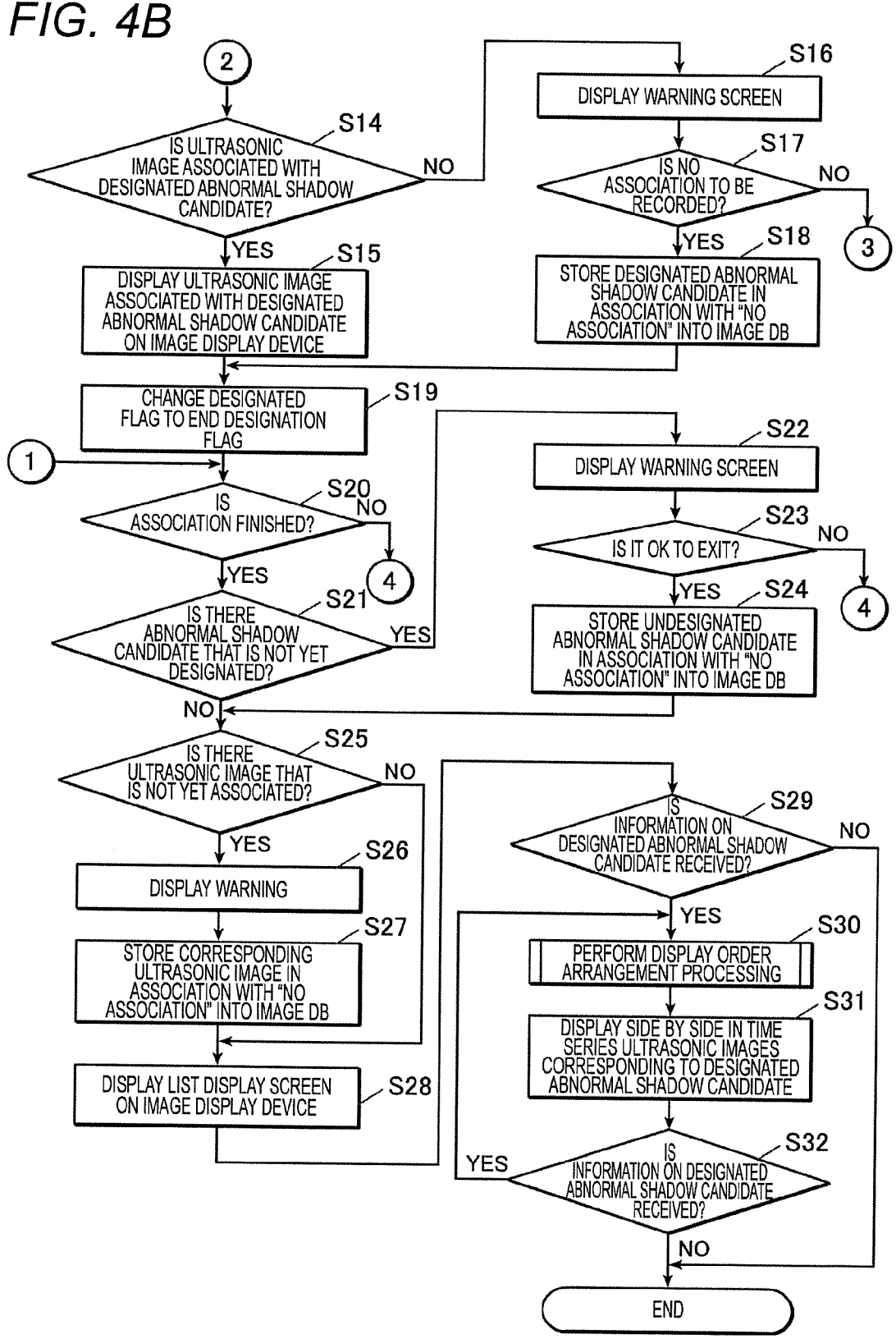
FIG. 4B is a flowchart illustrating the association processing executed by the control unit illustrated in FIG. 2.

FIGS. 4A and 4B are flowcharts illustrating the association processing executed by the server device 3. The association processing is executed cooperatively by the control unit 31 and the program stored in the storage unit 35 when a predetermined operation on the viewer screen instructs to execute the association processing with the ultrasonic image from the image display device 4 while the breast X-ray image obtained in the examination to be processed is selected by the operation unit 42 from the selection screen displayed on the display unit 43 of the image display device 4 so that the display unit 43 displays the viewer screen on which various processings are performed on the selected breast X-ray image of the examination.

Here, the control unit 31 of the server device 3 generates a monitoring table 311 illustrated in FIG. 5 in the RAM at the start of the association processing to monitor the state of association between the abnormal shadow candidate detected from the breast X-ray image of the examination selected and the ultrasonic image. At the start of the association processing, a management table stored in the image DB 351 or the like is referenced to write in the monitoring table 311 the examination ID of the breast X-ray image (examination) selected to be subjected to the association processing, the UID of each breast X-ray image, and the identification information of each abnormal shadow candidate included in each breast X-ray image. Information is written under "designation flag" and "UID of the ultrasonic image to be associated" during the process of the association processing. Note that a designation flag=0 (undesignated flag) indicates that the abnormal shadow candidate is not designated to be associated, a designation flag=1 (designated flag) indicates that the abnormal shadow candidate is currently being designated to be associated, and a designation flag=2 (end designation flag) indicates that the abnormal shadow candidate is no longer designated to be associated. The designation flag=0 is set to the identification information of all the abnormal shadow candidates by default. Moreover, it is assumed that the ultrasonic image received by the communication unit 34 during the association processing is stored in a temporary storage area of the RAM.

First, the control unit 31 refers to the image DB 351 and determines whether or not the breast X-ray image of the examination selected to be processed is the latest among medical images obtained by imaging the same site (breast in this case) of the same patient and is imaged within a predetermined period before this day (step S1). The control unit 31 proceeds to processing in step S4 upon determining that the breast X-ray image of the examination selected to be processed is the latest among the medical images obtained by imaging the same site of the same patient and is imaged within the predetermined period before this day (step S1; YES).

Upon determining, on the other hand, that the breast X-ray image of the examination selected to be processed is not the latest among the medical images obtained by imaging the same site of the same patient or is imaged before the predetermined period (step S1; NO), the control unit 31 generates image information of a warning screen (not shown) notifying that the breast X-ray image of the examination is not the latest one or that a predetermined period or longer has elapsed since the image was imaged, transmits the information to the image display device 4 through the communication unit 34, and causes the image display device 4 to display the warning screen (step S2).

The warning screen displays a warning message stating "The breast X-ray image of the examination selected is not the latest (or imaged ○ days or more before this day). Do you want to perform association?" as well as an OK button to instruct execution of the association and an NG button to instruct that the association is not to be executed. Once the OK button or the NG button is depressed by using the operation unit 42, the image display device 4 transmits the operation information to the server device 3.

The control unit 31 proceeds to processing in step S4 when receiving the instruction to execute the association from the image display device 4 through the communication unit 34 (step S3; YES). The control unit 31 ends the association processing when receiving the instruction to not execute the association from the image display device 4 through the communication unit 34 (step S3; NO).

In step S4, the control unit 31 generates screen information of an association screen 431 on which the breast X-ray image of the examination selected is associated with an ultrasonic image to be newly created, transmits the information to the image display device 4 through the communication unit 34, and causes the image display device 4 to display the association screen 431 (step S4).

Figure 6:
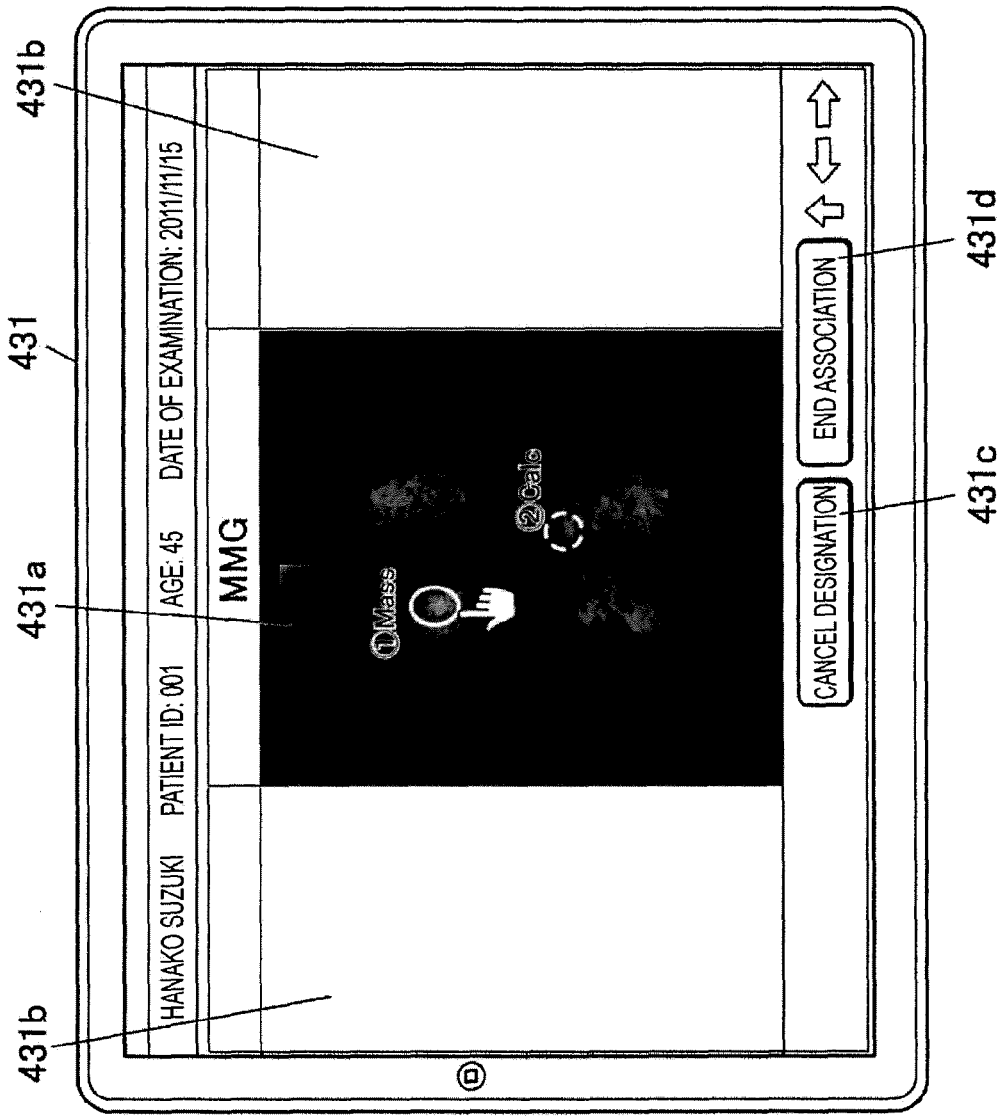
FIG. 6 is a diagram illustrating an example of an association screen.

FIG. 6 illustrates an example of the association screen 431. As illustrated in FIG. 6, the association screen 431 is provided with a breast X-ray image display area 431a and ultrasonic image display areas 431b (separately for right and left breasts). In the mammography examination, the image generation device 1 usually generates two breast X-ray images for each of right and left breasts by imaging each of the right and left breasts of one patient in the oblique direction (MLO) and the vertical direction (CC) for the total of four times. The breast X-ray image display area 431a displays an image (upper part in FIG. 6) in which right and left MLO images are arranged side by side with the thoratic walls put together and an image (lower part in FIG. 6) in which right and left CC images are arranged side by side with the thoratic walls put together. Moreover, each image displayed includes an annotation indicating the position of the abnormal shadow candidate based on the abnormal shadow candidate information corresponding to each image, so that a medical technologist or the like who performs the ultrasound examination uses the operation unit 42 to designate the abnormal shadow candidate to be subjected to the ultrasound examination from the breast X-ray image displayed in the breast X-ray image display area 431a. Specifically, the medical technologist or the like uses the operation unit 42 to designate two areas when he can locate the same abnormal shadow candidate in the MLO image and the CC image being displayed or designate one area when the abnormal shadow candidate can be located in only one of the images.

Moreover, the association screen 431 is provided with a "cancel designation" button 431c used to give an instruction to cancel the designation of the abnormal shadow candidate and an "end association" button 431d used to give an instruction to end the association processing.

When the operation unit 42 is used to designate the abnormal shadow candidate in the breast X-ray image displayed on the association screen 431, the image display device 4 employs the communication unit 44 to transmit information on the designated abnormal shadow candidate (position information or identification information but the identification information in this case) as operation information to the server device 3.

The server device 3 determines whether or not the information on the abnormal shadow candidate designated in the image display device 4 is received by the communication unit 34 (step S5). When determining that the information on the abnormal shadow candidate designated in the image display device 4 is received by the communication unit 34 (step S5; YES), the control unit 31 sets "1" under the column "designation flag" corresponding to the identification information of the abnormal shadow candidate received, namely the identification information of the designated abnormal shadow candidate, in the monitoring table 311 (step S6) and then stands by for the communication unit 34 to receive the ultrasonic image (step S7).

When determining that the information of the designated abnormal shadow candidate is not received from the image display device 4 by the communication unit 34 (step S5; NO), the control unit 31 proceeds to processing in step S20.

After designating the abnormal shadow candidate in the image display device 4, the person performing the examination uses the ultrasonic diagnosis device 5 to perform the ultrasound examination on the location of the designated abnormal shadow candidate of the breast of the same patient (image a tomogram of the location of the designated abnormal shadow candidate). Specifically, the person performing the examination performs scanning by placing the ultrasonic probe of the ultrasonic diagnosis device 5 over the location of the abnormal shadow candidate designated, takes in the image while performing a freeze operation, and then generates the ultrasonic image. A body mark indicating the examined position (imaging position) is recorded in the generated ultrasonic image, which is then transmitted to the server device 3.

The body mark is recorded according to a manual operation by the person performing the examination. When the person performing the examination uses the operation unit of the ultrasonic diagnosis device 5 to select a template image of the body mark (either one of the right and left breasts), a position on which the body mark is superposed in the ultrasonic image, and a position in which a probe mark is placed, for example, the body mark in which the selected probe mark is placed is recorded in the selected position of the ultrasonic image (written in the image).

Figure 7A:
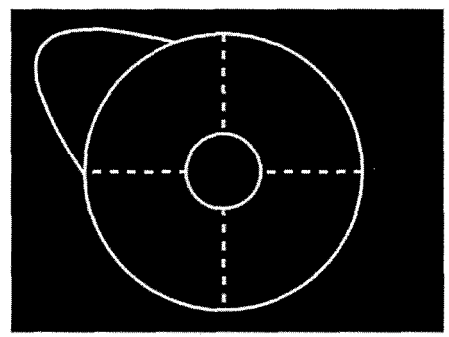
FIG. 7A is a template image of a body mark of a right breast.
Figure 7B:
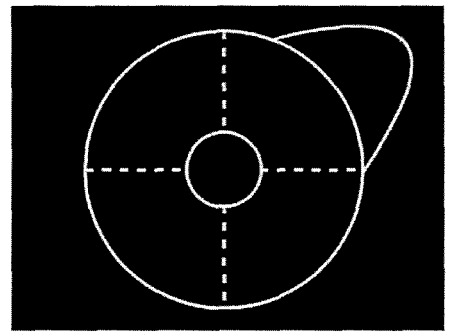
FIG. 7B is a template image of a body mark of a left breast.
Figure 7C:
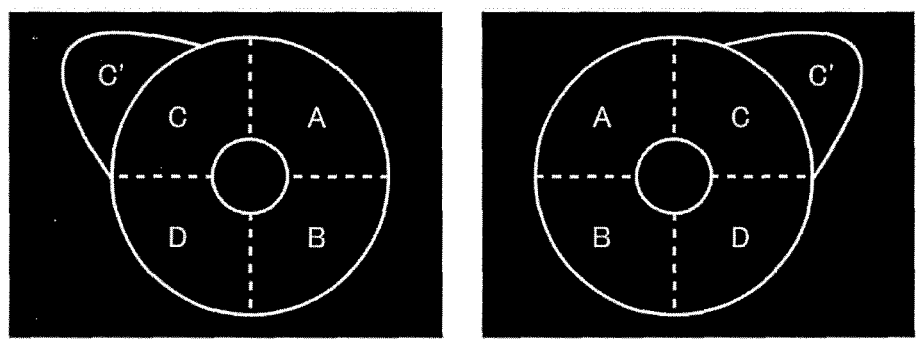
FIG. 7C is a set of diagrams illustrating areas in each of the right and left template images.
Figure 7D:
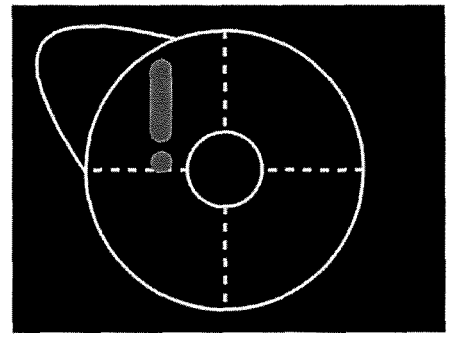
FIG. 7D is a diagram illustrating a body mark in which a probe mark is placed.

FIG. 7A illustrates the template image of the body mark of the right breast. FIG. 7B illustrates the template image of the body mark of the left breast. As illustrated in FIG. 7C, each of the template images illustrated in FIGS. 7A and 7B is divided into five areas including A, B, C, D, and C', each of which is associated with the position information. FIG. 7D illustrates the body mark on which the probe mark is superposed.

The body mark for each of the right and left breasts schematically illustrates each breast viewed from the front and is an image used to superpose thereon and display the probe mark indicating the position (examined position) of the area subjected to the ultrasound examination. An outer circle of the body mark represents a position of the breast, while a center circle represents a position of the nipple. The area A represents an area corresponding to an upper inner part of the breast, the area B represents an area corresponding to a lower inner part of the breast, the area C represents an area corresponding to an upper outer part of the breast, and the area D represents an area corresponding to a lower outer part of the breast. The area C' adjacent to the area C represents an underarm. The body mark has the same form as a schematic front image (refer to FIGS. 12A and 12E) on which a clinical position of the abnormal shadow candidate is superposed, where an area to which the same name is assigned indicates the same area of the breast. The clinical position refers to a position when a human body is viewed from the front. The body mark in which the probe mark is placed serves as clinical position information indicating the position (examined position) of the area subjected to the ultrasound examination when the breast is viewed from the front.

Referring back to FIG. 4A, once the communication unit 34 receives the ultrasonic image from the ultrasonic diagnosis device 5 (step S7; YES), the control unit 31 executes the collation processing between the abnormal shadow candidate and the examined position (step S8).

FIG. 8 is a flowchart illustrating the collation processing between the abnormal shadow candidate and the examined position executed in step S8.

The control unit 31 first executes processing of estimating the clinical position of the abnormal shadow candidate (step S800). Note that this processing may be performed when the ultrasonic image is received for the first time after designation. In the mammography examination, the image generation device 1 usually generates two breast X-ray images for each of the right and lefts breasts by imaging the breasts of a patient who is standing and whose breasts are subjected to pressure. On the other hand, the ultrasound examination is performed by placing the ultrasonic probe in a part of the breast that is not subjected to pressure while the patient is in a dorsal position. Accordingly, what is estimated in step S800 is the position, namely the clinical position, of the abnormal shadow candidate designated in the breast X-ray image at the time of the ultrasound examination.

FIG. 9 is a flowchart illustrating the processing of estimating the clinical position of the abnormal shadow candidate executed in step S800.

The control unit 31 first acquires an imaging angle included in the accompanying information of each breast X-ray image to be processed (the breast X-ray image in which the abnormal shadow candidate is designated between the X-ray images of the right and left breasts) that is displayed on the association screen 431 of the image display device 4 (step S8000). The imaging angle is an angle at which the image generation device 1 is tilted at the time of imaging the breast X-ray image (an angle in the direction in which the X-ray is emitted). The image generation device 1 by default includes a radiation source emitting the X-ray, a subject bed on which the subject is placed, and an FPD detecting the X-ray transmitted through the subject that are arranged vertically in this order but, in imaging the MLO image, these parts are integrally tilted by the angle according to the breast being the subject. Note that the imaging angle is 0° at the time of imaging the CC image since the image generation device 1 performs the imaging in the default state without being tilted.

Figure 10A:
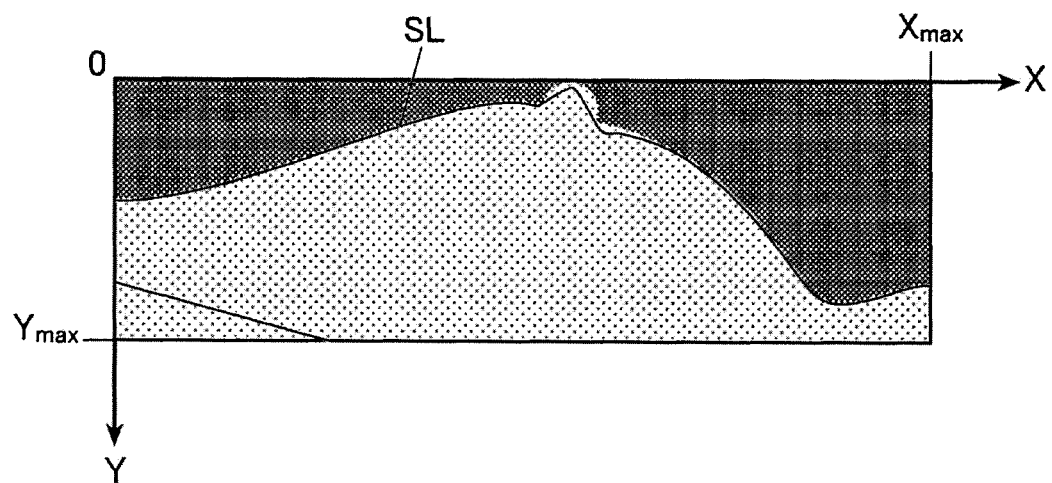
FIG. 10A is a diagram illustrating coordinates of a breast X-ray image.

Next, the control unit 31 detects a skin line and the nipple from each breast X-ray image to be processed (the MLO image and the CC image) (step S8001). Here, as illustrated in FIG. 10A, the position of each pixel in each breast X-ray image is represented by coordinates (X, Y) where an X axis corresponds to a top-bottom direction of the breast in the breast X-ray image and a Y axis corresponds to a direction perpendicular to the X axis. Moreover, a pixel value of the coordinates (X, Y) is represented as V (X, Y), a coordinate at an end of the image in the X axis direction is represented as Xmax, and a coordinate at an end of the image in the Y axis direction is represented as Ymax.

In step S8001, the control unit 31 first performs filtering processing with a Sobel filter on each pixel in each breast X-ray image to be processed as a pixel of interest. The control unit 31 then performs a search in the Y direction for each X coordinate (0 to Xmax) of the breast X-ray image to which the Sobel filter is applied, and extracts a coordinate (S) that results in the maximum V (X, Y) as an edge of each X coordinate. This extracted edge forms a skin line SL which is a boundary between the breast area and an area outside the breast.

Figure 10B:
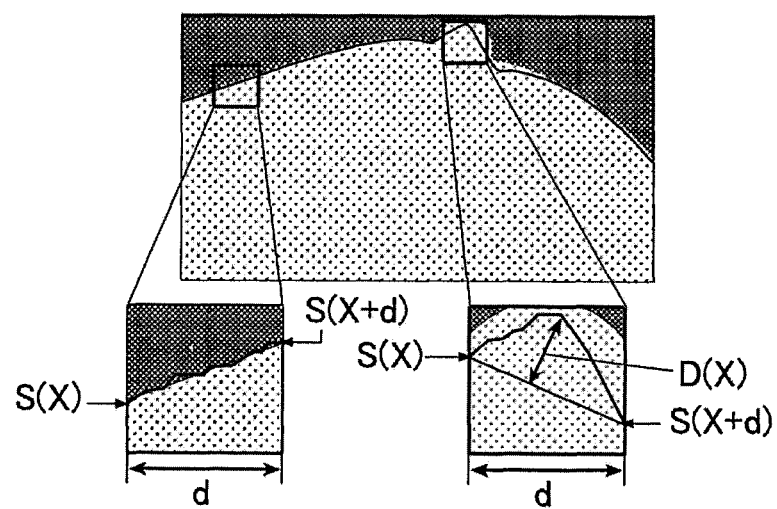
FIG. 10B is a diagram illustrating detection of a nipple position.

Next, as illustrated in FIG. 10B, the control unit 31 calculates for each point S (X) on the skin line SL a distance D between a straight line connecting S (X) and S (X+d (where d is 10, for example)) and each point between S (X) and S (X+d) (S (X+1), S (X+2) . . . S (X+d−1)), and then detects as the nipple position the position of S (X) having the largest maximum value D (X) of the calculated distance D.

Figure 11:
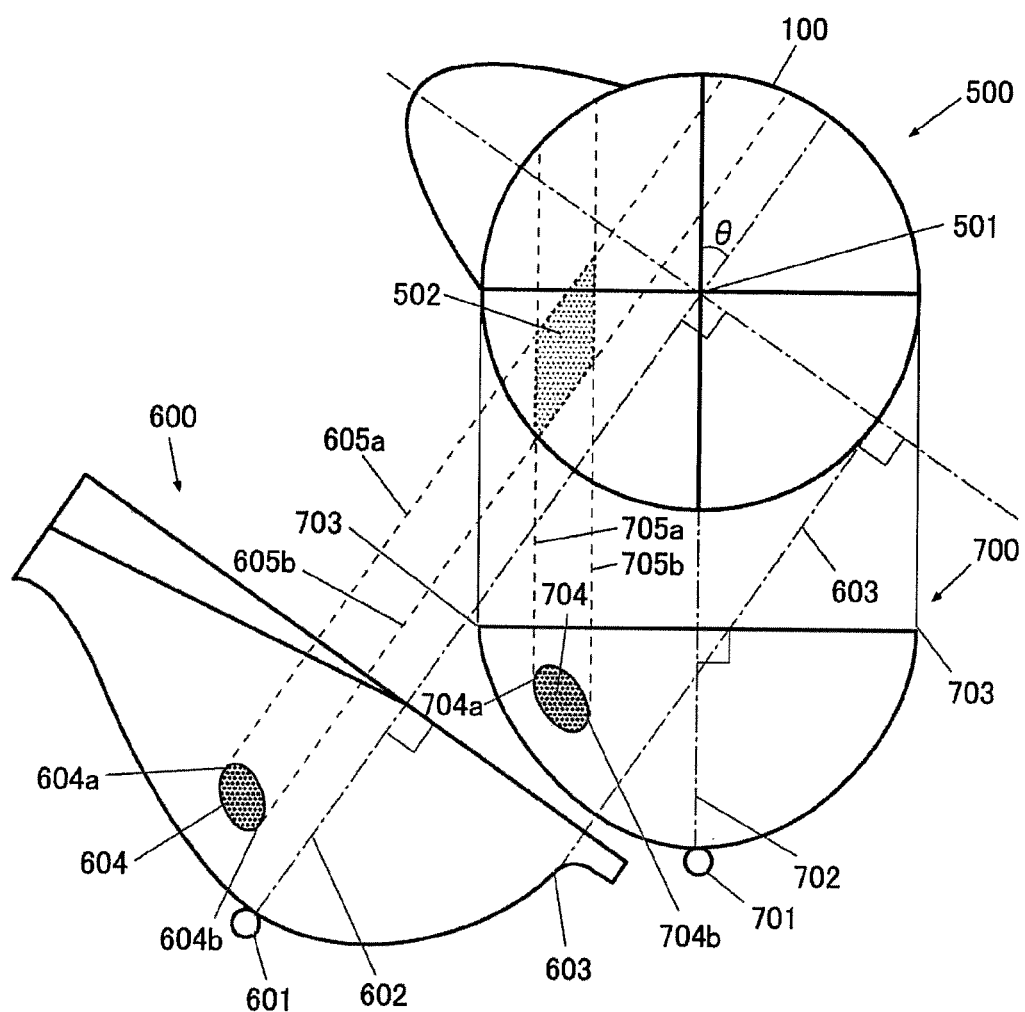
FIG. 11 is a diagram illustrating a method of generating clinical position information on an abnormal shadow candidate in a breast X-ray image.

Next, as illustrated in FIG. 11, the control unit 31 disposes a schematic front image of the breast (indicated by reference numeral 500 in FIG. 11), an MLO image (indicated by reference numeral 600 in FIG. 11), and a CC image (indicated by reference numeral 700 in FIG. 11) on the RAM on the basis of an angular difference θ[°] between the imaging angle at the time of imaging the MLO image and the imaging angle at the time of imaging the CC image (step S8002). Note that θ[°] corresponds with the imaging angle at the time of imaging the MLO image.

Figure 12A:
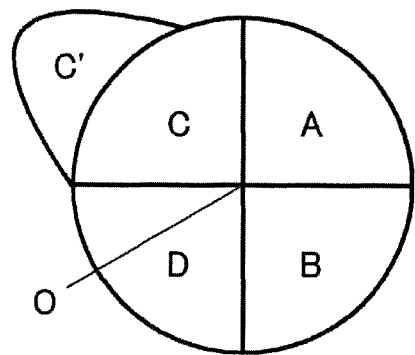
FIG. 12A is a schematic front image of the right breast.
Figure 12B:
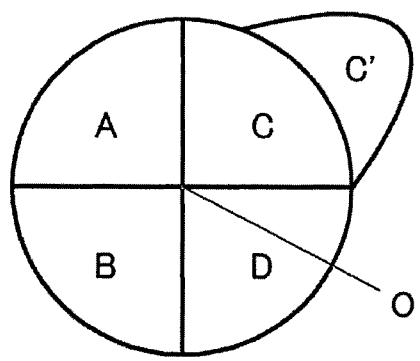
FIG. 12B is a schematic front image of the left breast.

FIG. 12A illustrates an example of the schematic front image of the right breast, and FIG. 12B illustrates an example of the schematic front image of the left breast. The schematic front image of each of the right and left breasts schematically illustrates the state of each breast viewed from the front, and is an image used to superpose thereon and display the clinical position of the abnormal shadow candidate. A circle in the schematic front image represents the breast while a center O represents the nipple position. An area A represents the area corresponding to the upper inner part of the breast, an area B represents the area corresponding to the lower inner part of the breast, an area C represents the area corresponding to the upper outer part of the breast, and an area D represents the area corresponding to the lower outer part of the breast. An area C' adjacent to the area C represents the underarm. This schematic front image of the breast has the same form as the body mark (refer to FIGS. 7A to 7D) on which the probe mark is superposed, the probe mark indicating the position (examined position) of a part of the breast being examined that is recorded in the ultrasonic image obtained by the ultrasound diagnosis.

As illustrated in FIG. 11, the schematic front image 500 is disposed first on the RAM in step S8002. Then, the MLO image 600 and the CC image 700 are disposed such that each of a perpendicular line 602 drawn from a nipple 601 of the MLO image 600 down to the thoratic wall and a perpendicular line 702 drawn from a nipple 701 of the CC image 700 down to the thoratic wall passes a nipple 501 of the schematic front image 500 and that an angular difference between the two perpendicular lines equals the angular difference θ[°] between the imaging angle at the time of imaging the MLO image and the imaging angle at the time of imaging the CC image. That is, each of the MLO image 600 and the CC image 700 is disposed while tilted from the schematic front image 500 by the imaging angle.

The control unit 31 thereafter increases or decreases the size of the MLO image 600 and the CC image 700 in accordance with the size of the schematic front image 500 (step S8003). Specifically, the CC image 700 is increased or decreased in size such that both ends 703 of the breast area correspond with both ends of the circle of the schematic front image 500 while the perpendicular line 702 drawn from the nipple 701 down to the thoratic wall intersects with the nipple 501 of the schematic front image 500. The MLO image 600 is increased or decreased in size such that a perpendicular line 603 drawn from a lower end of the breast area to the thoratic wall comes in contact with the circle of the schematic front image 500 while the perpendicular line 602 drawn from the nipple 601 down to the thoratic wall intersects with the nipple 501 of the schematic front image 500. Note that the both ends 703 of the breast area in the CC image 700 as well as the lower end of the breast area in the MLO image 600 can be specified on the basis of the skin line being detected.

The control unit 31 then projects each of an abnormal shadow candidate 604 in the MLO image 600 and an abnormal shadow candidate 704 in the CC image 700 onto the schematic front image 500 and estimates the position of the area, in which the projected abnormal shadow candidates overlap, to be the clinical position (step S8004). Specifically, the control unit first draws straight lines 605a and 605b perpendicular to the thoratic wall from a head end 604a and a tail end 604b of the abnormal shadow candidate 604 in the MLO image 600, respectively, and projects a belt-like area enclosed with the straight lines 605a and 605b onto the schematic front image 500. Likewise, the control unit draws straight lines 705a and 705b perpendicular to the thoratic wall from an outer end 704a and an inner end 704b of the abnormal shadow candidate 704 in the CC image 700, respectively, and projects a belt-like area enclosed with the straight lines 705a and 705b onto the schematic front image 500. Accordingly, an area 502 in which the two projected areas overlap is estimated as the clinical position of the abnormal shadow candidate. Note that the belt-like area is estimated as the clinical position of the abnormal shadow candidate when the abnormal shadow candidate is designated from either the MLO image or the CC image. The schematic front image 500 including the clinical position (a parallelogram or the belt-like area) serves as the clinical position information of the abnormal shadow candidate.

Referring back to FIG. 8, the control unit 31 after finishing the processing in step S800 extracts the body mark and the probe mark from the ultrasonic image received in step S7 in FIG. 4A (step S801).

In step S801, the control unit 31 first converts the received ultrasonic image into a gray scale image. Here, the ultrasonic image is a B-mode image formed of a signal value of three color channels corresponding to R (red), G (green), and B (blue). The ultrasonic image can be converted into the gray scale image by employing a typical conversion method. Where "I" is the signal value of each pixel after converting the ultrasonic image, the conversion can be performed by using (Expression 1) below, for example.

$$I=(R+G+B)/3 \quad \text{(Expression 1)}$$

Here, "R" is the signal value of the red channel of each pixel in the input ultrasonic image, "G" is the signal value of the green channel of each pixel in the input ultrasonic image, and "B" is the signal value of the blue channel of each pixel in the input ultrasonic image.

Next, the control unit 31 reads the template image of the body mark of the right breast (refer to FIG. 7A) and the template image of the body mark of the left breast (refer to FIG. 7B) that are stored in the storage unit 35, performs template matching processing of searching for each template image within the ultrasonic image, and extracts the body mark. That is, the control unit calculates a cross correlation value of a target area, which is compared with the template image, with the template image while moving the target area within the ultrasonic image area, and extracts as the body mark area an area in which the cross correlation value equals a predetermined value or higher and is the highest. A zero mean normalized cross correlation Rzncc illustrated in (Expression 2) can be used as the cross correlation value, for example.

[Equation 1]

Note that one body mark is recorded in each ultrasonic image. Therefore, the area in which the cross correlation value equals the predetermined value or higher within the ultrasonic image area is present in either one of the template images, whereby one can tell whether the body mark is in the right or left image. The control unit 31 stores right/left information of the body mark in the RAM.

Next, the control unit 31 extracts the probe mark. Although the ultrasonic image is a color image, the ultrasonic image itself is achromatic where the difference in the signal values of R, G, and B in each pixel is small. On the other hand, the probe mark on the body mark recorded in the ultrasonic image has a chromatic color to stand out in the ultrasonic image. Accordingly, the control unit picks up a pixel that is not an achromatic pixel which has a signal difference between R-G and G-B of each color channel in each pixel equal to 32 or less in 8 bits. Among the pixels being picked up, an area corresponding to a pixel within the area of the extracted body mark is extracted as the area of the probe mark.

Once the body mark and the probe mark are extracted, the control unit 31 calculates an area ratio of the probe mark occupying each of the five divided areas of the body mark (step S802). Here, as illustrated in FIG. 7C, the template image of the body mark is divided into the five areas including A, B, C, D, and C', each of which is associated with the position information. Accordingly, the image of the body mark extracted from the ultrasonic image is superposed on the template image with the known area information so that the five divided areas of the body mark are specified to calculate an area of the probe mark occupying each area and to calculate the area ratio. The area can be found by counting the number of pixels, for example. The area having the largest area ratio is where the area occupied by the probe mark is the largest, namely where the probe mark is mainly located.

Next, the control unit 31 calculates an area ratio of the clinical position of the abnormal shadow candidate (the projected area in step S8004) estimated to occupy each of the five divided areas of the schematic front image (step S803), and compares the right/left information as well as an area having the largest area ratio calculated between the body mark and the schematic front image (step S804). The right/left information of the body mark is stored in the RAM of the control unit 31 as described above. The right/left information of the schematic front image can be acquired from the accompanying information of the breast X-ray image which includes the abnormal shadow candidate being designated.

Figure 13:
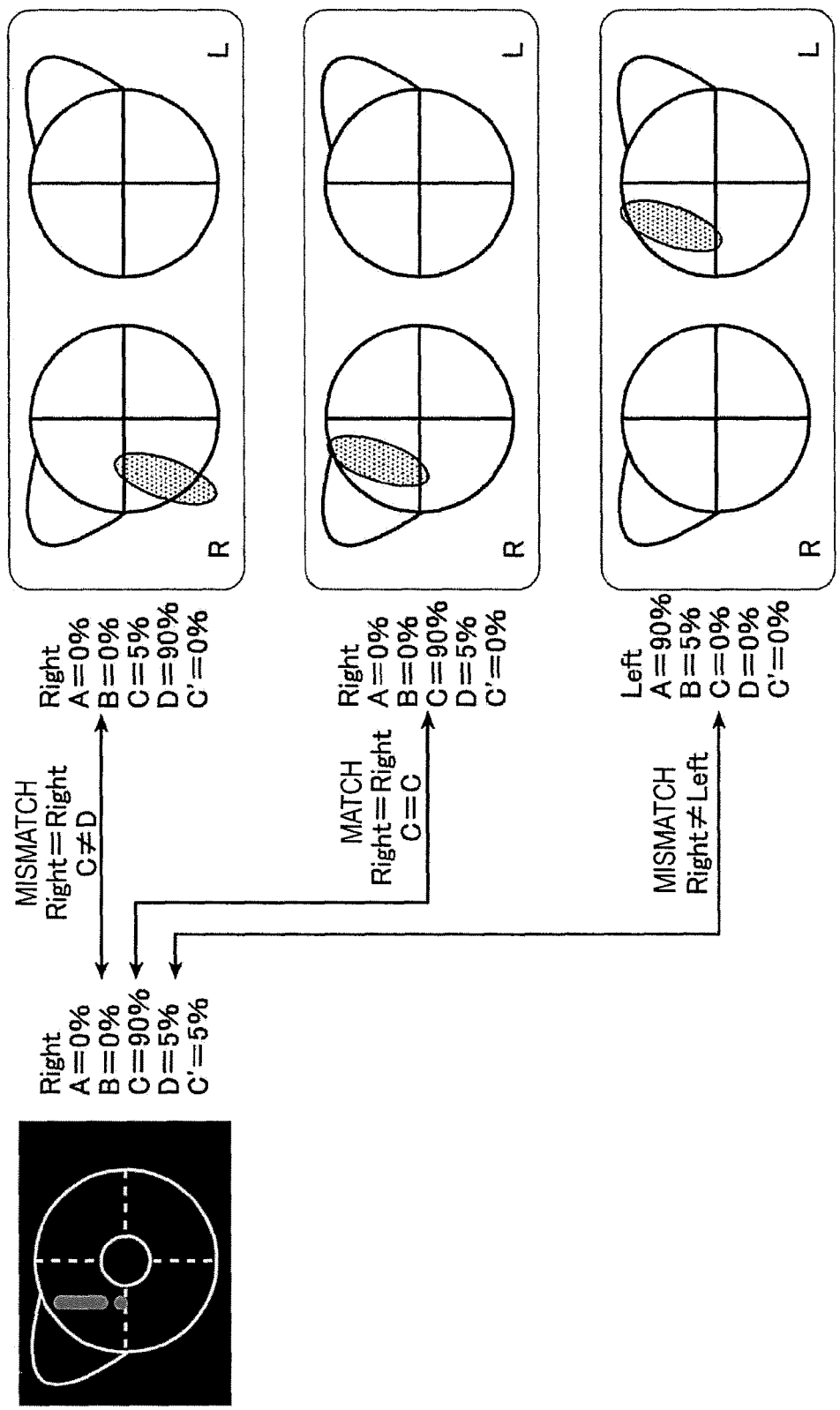
FIG. 13 is a diagram illustrating the collation processing performed between the abnormal shadow candidate and the examined position as illustrated in FIG. 8.

The right/left information of the body mark illustrated in FIG. 13 is "Right", for example, and the area ratio of the probe mark is the largest in the area C. In other words, the probe mark illustrated in the body mark is predominantly positioned in the area C. Regarding the clinical position information illustrated in the upper tier in FIG. 13, on the other hand, the area ratio of the projected area of the abnormal shadow candidate is the largest in the area D. In other words, the clinical position of the abnormal shadow candidate is predominantly positioned in the area D. Accordingly, a mismatch is the result of comparison between the two images. The right/left information of the clinical position information illustrated in the lower tier in FIG. 13 is "Left", whereby the comparison result is a mismatch since the right/left information does not correspond with that of the body mark. On the other hand, the comparison result is a match between the body mark and the clinical position information illustrated in the middle tier in FIG. 13 because the right/left information of the clinical position information corresponds with that of the body mark and, at the same time, the area C is the area with the largest area ratio in both the body mark and the clinical position information (that is, the position of the probe mark corresponds with the position of the projected area of the abnormal shadow candidate).

Now proceeding to processing in step S9 in FIG. 4A, the control unit 31 determines whether or not the clinical position information of the abnormal shadow candidate matches OK with the clinical position information of the examined position (step S9). When determining that the match is performed OK (step S9; YES), the control unit 31 proceeds to processing in step S12.

When determining that the match is not performed OK (step S9; NO), the control unit 31 generates image information of a warning screen (not shown) notifying on the association screen 431 that the clinical position information of the abnormal shadow candidate designated does not match the clinical position information of the examined position of the ultrasonic image received, transmits the information to the image display device 4 through the communication unit 34, and causes the image display device 4 to display the warning screen (step S10).

The warning screen displays a warning message stating "The abnormal shadow candidate designated does not match the examined position of the ultrasonic image received. The body mark may be designated incorrectly. Do you want to perform association?" as well as an OK button to instruct execution of the association and an NG button to instruct that the association is not to be executed. Once the OK button or the NG button is depressed by using the operation unit 42, the image display device 4 transmits the operation information to the server device 3.

The control unit 31 proceeds to processing in step S12 when receiving the instruction to execute the association from the image display device 4 through the communication unit 34 (step S11; YES).

In step S12, the designated abnormal shadow candidate is stored in association with the ultrasonic image received in step S7 into the image DB 351 (step S12), followed by processing in step S13. Specifically, the control unit adds a record of the examination ID of the selected examination to the ultrasonic image association table 353 and stores therein the identification information of the designated abnormal shadow candidate in association with the UID stored in the header of the ultrasonic image being received. The same information is stored in the monitoring table 311 as well. Moreover, the received ultrasonic image is stored in the image area of the image DB 351, so that the file name and storage location of the image are stored in association with the record of the breast X-ray image of the examination selected.

On the other hand, the control unit 31 proceeds to processing in step S13 when receiving the instruction to not execute the association from the image display device 4 through the communication unit 34 (step S11; NO).

In step S13, the control unit 31 determines whether or not operation information which gives the instruction to cancel designation is received from the image display device 4 through the communication unit 34 (step S13). The control unit 31 returns to the processing in step S7 and repeats the processing in each of steps S7 to S13 when determining that the operation information which gives the instruction to cancel the designation is not received from the image display device 4 (step S13; NO).

When determining that the operation information which gives the instruction to cancel the designation is received from the image display device 4 (step S13; YES), the control unit 31 refers to the image DB 351 and determines whether or not the ultrasonic image is associated with the designated abnormal shadow candidate (step S14). When determining that the ultrasonic image is associated with the designated abnormal shadow candidate (step S14; YES), the control unit 31 generates screen information of the association screen 431, on which the ultrasonic image associated with the designated abnormal shadow candidate is displayed in the ultrasonic image area 341*b*, transmits the generated information to the image display device 4 through the communication unit 34, causes the display unit 43 to display the ultrasonic image associated with the designated abnormal shadow candidate (step S15), and proceeds to processing in step S19.

Figure 14:
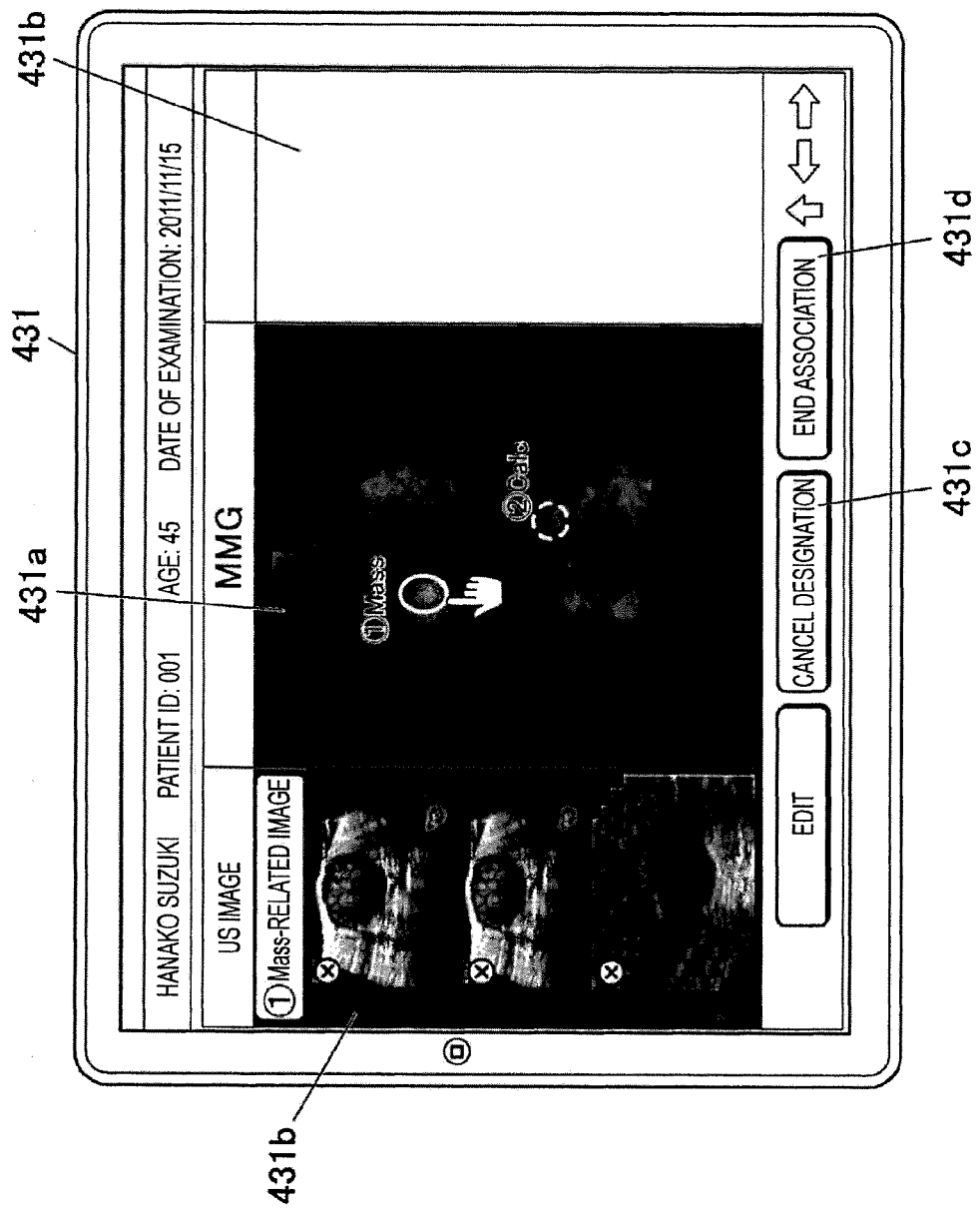
FIG. 14 is a diagram illustrating an example of the association screen displayed on the image display device by processing performed in step S15 of FIG. 4B.

FIG. 14 illustrates an example of the association screen 431 displayed on the image display device 4 by the processing performed in step S15. In the association screen 431, the annotation displayed in the abnormal shadow candidate designated in step S5 is displayed while modified into a predetermined display (by changing color, for example), and the ultrasonic image associated with the abnormal shadow candidate is displayed in the ultrasonic image area 431*b*.

When determining in step S14 that the ultrasonic image is not associated with the designated abnormal shadow candidate (step S14; NO), the control unit 31 generates image information of a warning screen (not shown) notifying that the ultrasonic image is not associated with the designated abnormal shadow candidate on the association screen 431, transmits the information to the image display device 4 through the communication unit 34, and causes the image display device 4 to display the warning screen (step S16).

The warning screen displays a warning message stating "The ultrasonic image is not associated with the designated abnormal shadow candidate. Do you want to record no association?" as well as an OK button to record no association and an NG button which instructs to not record no association. Once the OK button or the NG button is depressed by using the operation unit 42, the image display device 4 transmits the operation information to the server device 3.

The control unit 31 returns to the processing in step S7 when receiving the instruction to not record no association from the image display device 4 through the communication unit 34 (step S17; NO).

When receiving the instruction to record no association from the image display device 4 through the communication unit 34 (step S17; YES), the control unit 31 stores, in the image DB 351, the designated abnormal shadow candidate in association with "no association" (step S18) and proceeds to processing in step S19. Specifically, the control unit adds a record of the selected examination ID to the ultrasonic image association table 353 and stores therein the identification information of the designated abnormal shadow candidate in association with "no association". The same information is stored in the monitoring table 311 as well.

In step S19, the control unit 31 changes the designated flag=1 in the monitoring table 311 to the end designation flag=2 (step S19). The control unit 31 then determines whether or not operation information indicating the end of association is received from the image display device 4 through the communication unit 34 (step S20). The control unit 31 returns to the processing in step S5 in FIG. 4A when determining that the operation information indicating the end of association is not received (step S20; NO).

When determining that the operation information indicating the end of association is received (step S20; YES), the control unit 31 determines whether or not there exists an abnormal shadow candidate that is not yet designated in the breast X-ray image of the examination selected (step S21). The control unit 31 proceeds to processing in step S25 when determining there exists no abnormal shadow candidate that is not yet designated (all abnormal shadow candidates are designated) (step S21; NO).

When determining there exists the abnormal shadow candidate that is not yet designated (step S21; YES), the control unit 31 generates image information used to display on the association screen 431 a warning screen (not shown) notifying that there exists the abnormal shadow candidate on which association is not yet performed, transmits the information to the image display device 4 through the communication unit 34, and causes the image display device 4 to display the warning screen (step S22).

The warning screen displays a warning message stating "There exists an abnormal shadow candidate that is not yet associated. Do you want to exit?" as well as an OK button which instructs to exit and an NG button which instruct not to exit, for example. Once the OK button or the NG button is depressed by using the operation unit 42, the image display device 4 transmits the operation information to the server device 3.

The control unit 31 returns to the processing in step S5 when receiving the instruction to not exit from the image display device 4 through the communication unit 34 (step S23; NO).

When receiving the instruction to exit from the image display device 4 through the communication unit 34 (step S23; YES), the control unit 31 records in the image DB 351 the undesignated abnormal shadow candidate in association with "no association" (step S24) and proceeds to processing in step S25. Specifically, the control unit in step S24 adds a record of the selected examination ID to the ultrasonic image association table 353 and stores therein the identification information of the designated abnormal shadow candidate in association with "no association". The same information is stored in the monitoring table 311 as well.

In step S25, the control unit 31 determines whether or not there exists an ultrasonic image that is not associated with the abnormal shadow candidate on record among the ultrasonic images received while the association processing is performed (step S25). The determination is made by searching for the ultrasonic image with the UID that is not associated with the abnormal shadow candidate in the monitoring table 311 among the ultrasonic images stored in the temporary storage area of the RAM, for example.

When determining there exists the ultrasonic image that is not associated with the abnormal shadow candidate on record (step S25; YES), the control unit 31 generates image information used to display on the association screen 431 a warning screen (not shown) notifying that there exists the ultrasonic image that is not associated with the abnormal shadow candidate on record, transmits the information to the image display device 4 through the communication unit 34, and causes the image display device 4 to display the warning screen (step S26). The warning screen displays a warning message stating "There exists an ultrasonic image that is not associated.", for example. The control unit 31 then records into the image DB 351 the ultrasonic image, which is not associated with the abnormal shadow candidate, in association with "no association" (step S27) and proceeds to processing in step S28. Specifically, the control unit adds a record of the selected examination ID to the ultrasonic image association table 353 and stores therein the UID of the corresponding ultrasonic image in association with "no association". Moreover, the ultrasonic image is stored in the image area of the image DB 351, so that the file name and storage location of the image are stored in association with the record of the breast X-ray image of the examination ID being selected.

The control unit 31 proceeds to processing in step S28 when determining there exists no ultrasonic image that is not associated with the abnormal shadow candidate on record (step S25; NO).

In step S28, the control unit 31 generates image information used to display the list display screen 432 on the image display device 4, transmits the information to the image display device 4 through the communication unit 34, and causes the image display device 4 to display the list display screen 432 (step S28).

Here, the ultrasonic image (current as well as past ones) stored in the image DB 351 includes various types of ultrasonic images (such as a B-mode image, a Doppler image, and an elastography image) of a plurality of abnormal shadow candidates accumulated for the number of times the examination is performed by looking at the same patient alone, as illustrated in FIG. 15A. FIG. 15A illustrates a case where there are two abnormal shadow candidates (abnormal shadow candidates 1 and 2), where as many as 14 images are stored for the two abnormal shadow candidates.

It is useful for the ultrasonic images obtained by examining a certain abnormal shadow candidate of a patient to be displayed side by side in a chronological order when one attempts to provide an explanation to the patient or the like, because the chronological display makes it easy to observe a chronological change of the abnormal shadow candidate. However, it is difficult to grasp the examined position in the ultrasonic image, causing large amounts of time and effort to display side by side the ultrasonic images obtained by examining the certain abnormal shadow candidate manually in the chronological order from among a number of ultrasonic images taken for one patient. Accordingly, in the present embodiment, the list display screen 432 displays a designated type of ultrasonic images side by side in time series from among the ultrasonic images corresponding to the designated abnormal shadow candidate.

Figure 16:
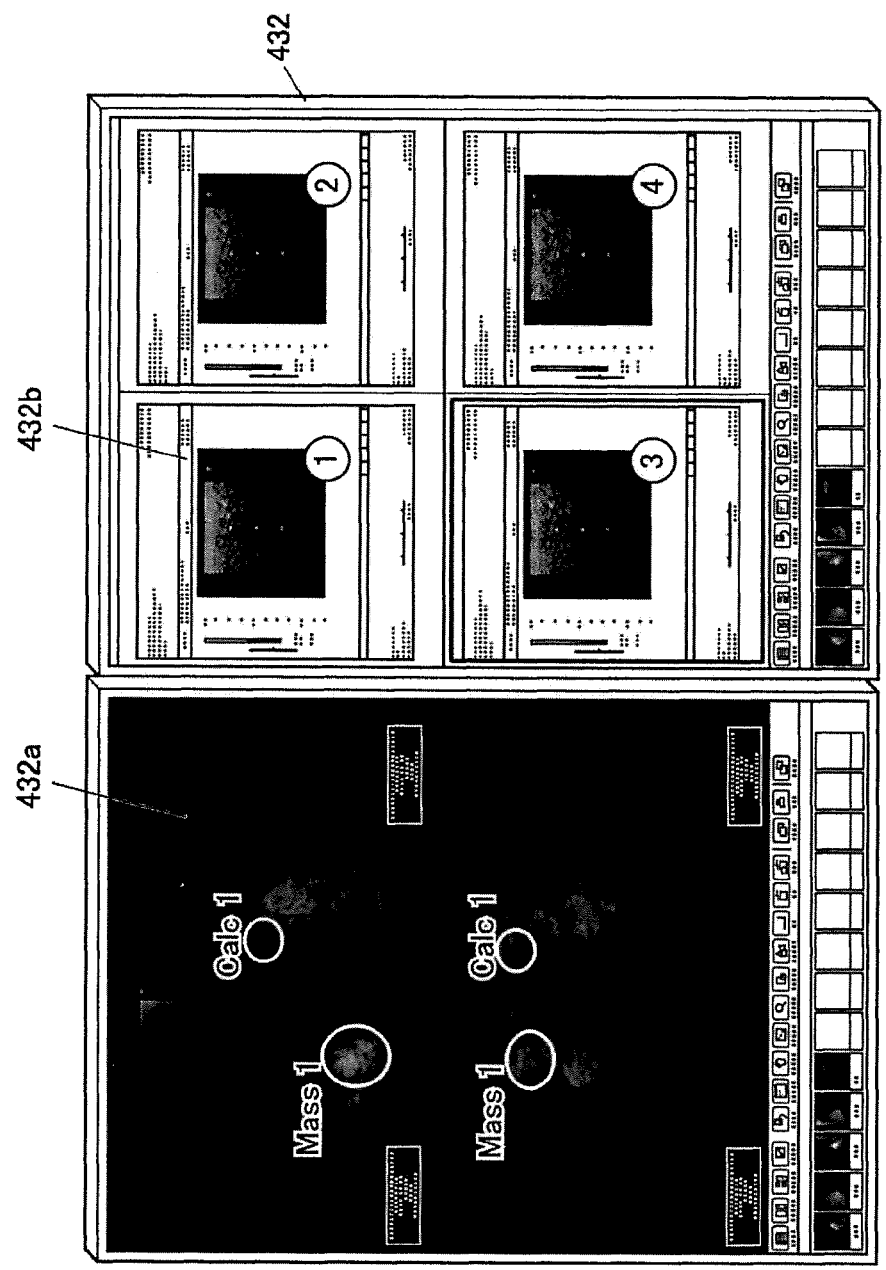
FIG. 16 is a diagram illustrating an example of a list display screen.

FIG. 16 illustrates an example of the list display screen 432. The list display screen 432 is provided with a breast X-ray image display box 432a and an ultrasonic image display box 432b. The breast X-ray image display box 432a displays an image in which the annotation is added to the abnormal shadow candidate in the breast X-ray image that is imaged in the mammography examination. The ultrasonic image display box 432b displays the ultrasonic image that is imaged in the ultrasound examination. Once the operation unit 42 is operated to designate the abnormal shadow candidate from the image displayed in the breast X-ray image display box 432a (a second designation unit), the control unit 41 transmits position information of the designated abnormal shadow candidate to the server device 3 through the communication unit 44, and gives an instruction to execute display order arrangement processing of arranging in time series the ultrasonic image corresponding to the designated abnormal shadow candidate.

The control unit 31 executes the display order arrangement processing (step S30) after the communication unit 34 receives information on the abnormal shadow candidate (position information or identification information, but the identification information in this case) designated in the image display device 4 (step S29; YES).

Figure 17:
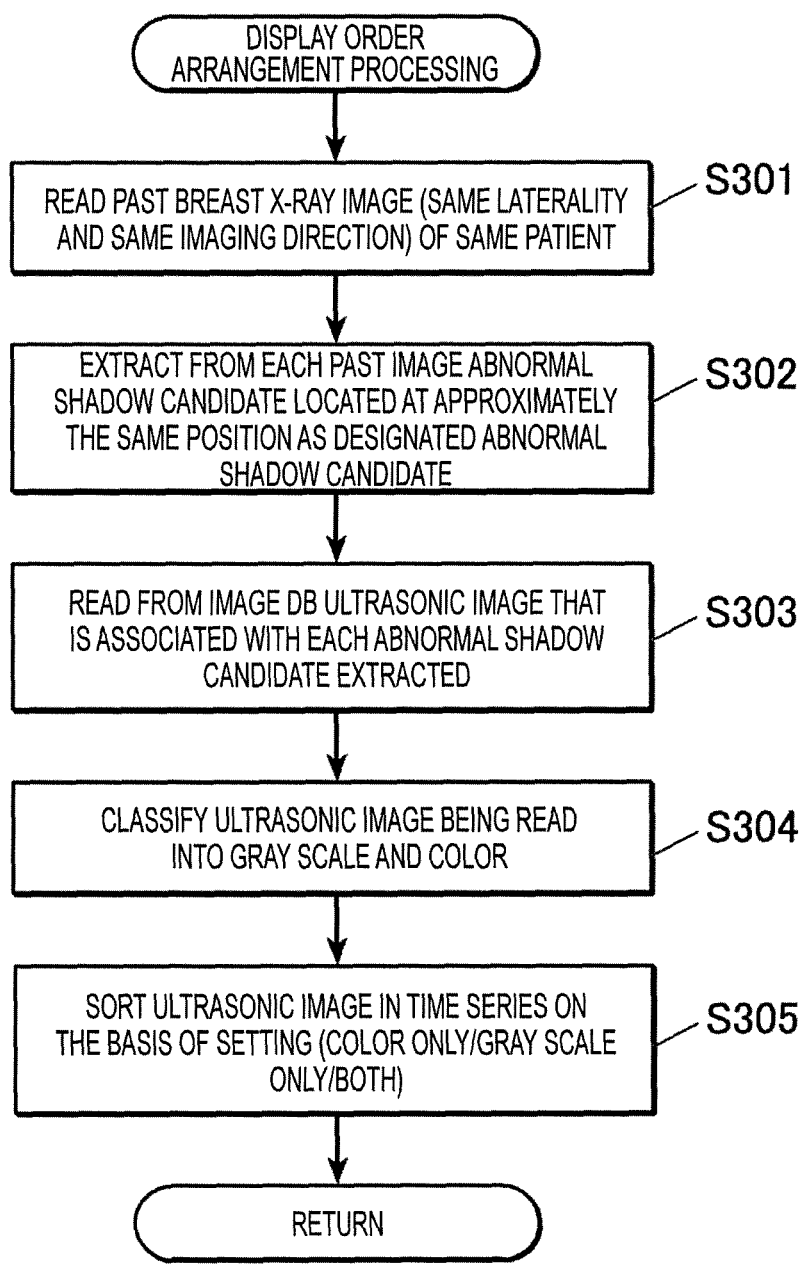
FIG. 17 is a flowchart illustrating the display order arrangement processing executed in step S30 of FIG. 4B.

FIG. 17 illustrates a flowchart of the display order arrangement processing executed in step S30.

In the display order arrangement processing, the control unit 31 first reads from the image DB 351 a breast X-ray image obtained in the past (referred to as a past image), which has the same right/left laterality and the imaging direction as that of the breast X-ray image in which the abnormal shadow candidate is designated, as well as the abnormal shadow candidate information of the past image from among the past images of the same patient (step S301). Note that the control unit may instead read from the image DB 351 a breast X-ray image obtained within a predetermined period in the past and the abnormal shadow candidate information of the X-ray image.

Next, the control unit 31 extracts from each past image being read an abnormal shadow candidate located at approximately the same position as the designated abnormal shadow candidate (step S302).

Figure 18:
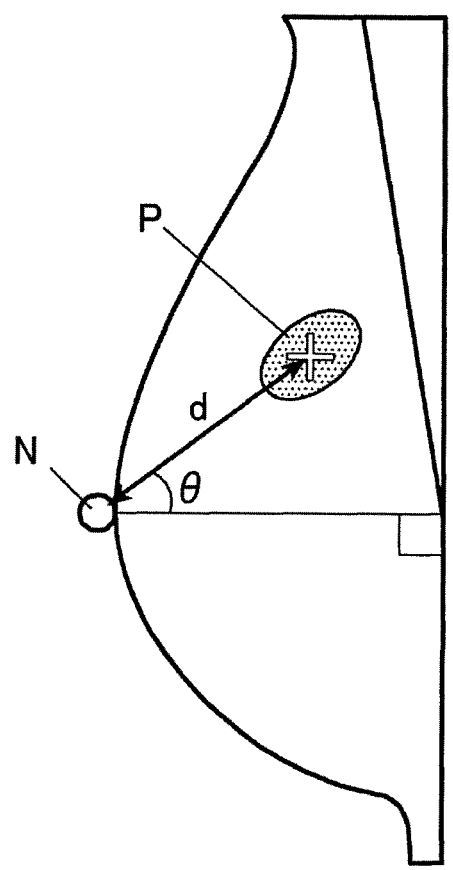
FIG. 18 is a diagram illustrating step S302 performed in FIG. 17.

Specifically, in step S302, the following processings (1) to (3) are performed on each past image being read in step S301 to extract, from the past image, the abnormal shadow candidate located at approximately the same position as the designated abnormal shadow candidate. (1) The nipple is detected first. The nipple is detected in the same manner as that described in step S8001 in FIG. 9, to which one may refer for description. (2) Next, as illustrated in FIG. 18, the position of a centroid of the abnormal shadow candidate (indicated by P in FIG. 18) is expressed in a polar coordinate system where a distance d is measured from the nipple (indicated by N in FIG. 18) to the centroid of the abnormal shadow candidate, and a perpendicular line drawn from the nipple N to the thoratic wall has an angle θ°. When one past image includes a plurality of abnormal shadow candidates, the centroid of each of abnormal shadow candidates P1 to Pn is expressed in the polar coordinate system. Note that the abnormal shadow candidate designated in step S29 is expressed in the polar coordinate system as well. (3) Next, the coordinates (d, θ) of the designated abnormal shadow candidate and the coordinates (d, θ) of each of the abnormal shadow candidates P1 to Pn are plotted in a two-dimensional feature space with d and θ (a coordinate space having d and θ axes) so that there is extracted, as the abnormal shadow candidate located at approximately the same position as the designated abnormal shadow candidate, an abnormal shadow candidate having an Euclidean distance which is equal to a predetermined threshold THd or less and the smallest with a point of the designated abnormal shadow candidate plotted in the aforementioned space.

Next, the control unit 31 refers to the association table in the image DB 351 to read the ultrasonic image associated with each abnormal shadow candidate extracted in step S302 (step S303) and classifies the read ultrasonic image group by the type (step S304).

Here, the ultrasonic image mainly includes the B-mode image, the Doppler image, and the elastography image. The B-mode image is an image having the proportion of the color area equal to approximately 0.3% to 0.5%, where a part corresponding to the subject is imaged in gray scale and a measured line and the body mark are imaged in color. The Doppler image is an image showing a blood flow signal of the subject in color, where the proportion of the color area in the image is approximately 8%. The elastography image is an image showing a degree of elasticity of the subject in color, where the proportion of the color area in the image is approximately 20%. The proportion of the color area can be found by (Expression 3) below.

The proportion of the color area=the number of pixels having a color component*the number of pixels in the entire area*100 (Expression 3)

In step S304, the acquired ultrasonic image is classified into the gray scale image (the B-mode image) and the color image (the Doppler image and the elastography image) on the basis of the proportion of the color area.

When the proportion of the color area is lower than a predetermined threshold TH (such as TH=1%), for example, the ultrasonic image is determined to be the gray scale image so that a color flag OFF is set to that ultrasonic image. The ultrasound image is determined to be the color image when the proportion of the color area equals the TH or higher, in which case a color flag ON is set to that ultrasonic image. Note that a pixel is determined to be a color pixel having the color component when the signal difference between R-G and G-B of each color channel is 32 or more (in 8 bits), whereas a pixel not satisfying the aforementioned condition can be determined as the gray scale image.

The control unit 31 then sorts past to present ultrasonic images of the designated abnormal shadow candidate according to the examination date and the setting of the type of the ultrasonic images (gray scale only, color only, and both) that are arranged in time series (step S305). When the gray scale only is set, for example, the B-mode images of the designated abnormal shadow candidate are sorted in time series as illustrated in FIG. 15B. When both the gray scale and the color are set, for example, the gray scale images and the color images are sorted separately in time series as illustrated in FIG. 15C. Note that the type of the ultrasonic images to be arranged in time series can be set by the image display device 4. When both the gray scale and the color are set, the gray scale the color are sorted separately in time series. Once the images are sorted, the control unit 31 ends the display order arrangement processing and proceeds to step S31 in FIG. 4B.

In step S31 in FIG. 4B, the control unit 31 generates screen information of the list display screen 432, displayed on which is a screen 432c displaying in the ultrasonic image display box 432b the ultrasonic image of the type being set in time series among the ultrasonic images corresponding to the abnormal shadow candidate designated in step S29 (corresponding substantially with the position information), transmits the information to the image display device 4 through the communication unit 34, and causes the display unit 43 to display the information (step S31).

Figure 19:
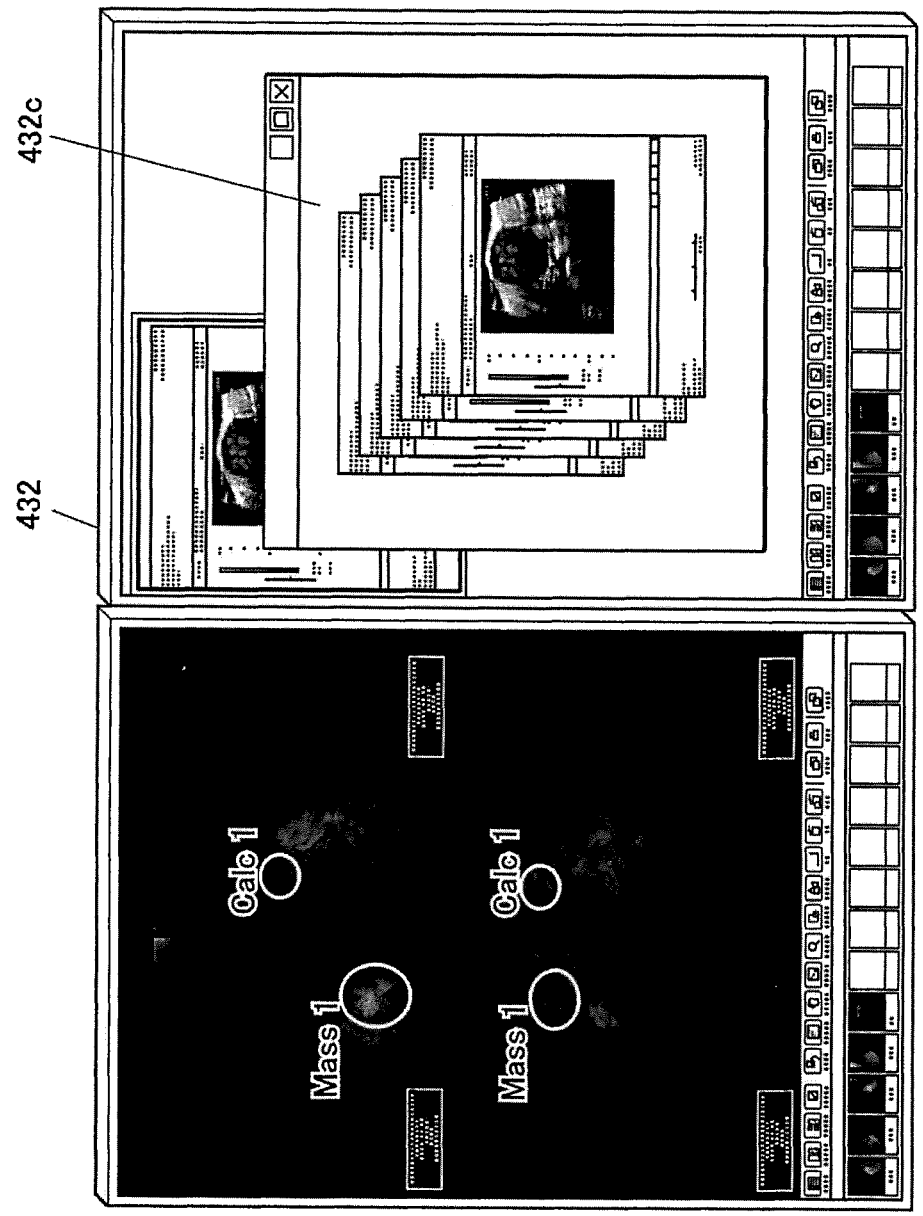
FIG. 19 is a diagram illustrating an example of a list display screen on which a screen displaying in time series an ultrasonic image relevant to an abnormal shadow candidate being designated is displayed.

FIG. 19 illustrates an example of the list display screen 432 on which the screen 432c displaying in time series the ultrasonic image corresponding to the abnormal shadow candidate being designated is displayed. Each image displayed on the screen 432c can be displayed in the foremost position by using the operation unit 42 to click the upper end of each image. Moreover, each image may be tiled (displayed in a non-overlapping manner) in time series on the screen 432c by using the operation unit 42 to click the screen 432c, for example.

The current to past ultrasonic images only corresponding to the abnormal shadow candidate designated in the breast X-ray image are displayed in time series as described above, whereby a person performing the examination or a doctor can easily observe the change in the abnormal shadow candidate over time.

One may use the operation unit 42 to designate another abnormal shadow candidate from the breast X-ray image display box 432a when he wishes to display in time series the ultrasonic images corresponding to the other abnormal shadow candidate.

The control unit 31 returns to step S30 and executes the processing in each of steps S30 and S31 after the communication unit 34 receives information on the other abnormal shadow candidate designated in the image display device 4 (step S32; YES). The control unit 31 ends the association processing when the information on the other abnormal shadow candidate is not received (step S32; NO).

According to the medical image system 100, as described above, the control unit 31 of the server device 3 performs the association between the abnormal shadow candidate and the ultrasonic image received when the breast X-ray image of the examination selected to be subjected to the association processing is an image suited for the association and the abnormal shadow candidate designated to be associated matches the clinical position information indicating the examined position in the ultrasonic image being received. Moreover, the control unit 31 monitors the association, outputs warning when the ultrasonic image is not associated with the abnormal shadow candidate, designation of which is canceled, and stores the designated abnormal shadow candidate in association with "no association" in the image DB 351 on the basis of the instruction from the image display device 4. When the instruction to end the association processing is made, the control unit 31 determines whether or not there exists the abnormal shadow candidate not being designated and, when there does, outputs the warning and stores the corresponding abnormal shadow candidate in association with "no association" in the image DB 351 on the basis of the instruction from the image display device 4. The control unit 31 further determines whether or not there exists the ultrasonic image not being associated and, when there does, outputs the warning and stores the undesignated abnormal shadow candidate in association with "no association" in the image DB 351 on the basis of the instruction from the image display device 4.

As a result, one can prevent images that are not to be associated with each other from being associated with each other when the ultrasonic image is associated with the abnormal shadow candidate in the breast X-ray image, and can allow the person performing the examination to recognize that there exists the abnormal shadow candidate or the ultrasonic image that is not associated when such candidate or image exists. Moreover, the abnormal shadow candidate or the ultrasonic image not being associated is stored in association with "no association" in the image DB 351 upon confirmation by the person performing the examination, whereby it can be made clear that the candidate or image is not associated by the person performing the examination. As a result, there can be prevented a decrease in the diagnostic efficiency caused by the abnormal shadow candidate in the breast X-ray image and the ultrasonic image not being associated with each other at the time of a diagnosis as well as an increase in the burden such as re-examination on both the hospital and the patient.

When the breast X-ray image selected to be associated is the latest among the breast X-ray images obtained by imaging the same subject site of the same patient and is imaged within the predetermined period, for example, the control unit 31 determines that the image is suited for association or otherwise outputs the warning, whereby one can prevent a case where the association is performed by using images that are not to be associated with each other because the clinical condition has possibly changed since the date the breast X-ray image is imaged, the date being apart from the date of imaging the ultrasonic image (this day).

Moreover, the control unit 31 estimates the clinical position information of the designated abnormal shadow candidate and, when the clinical position information of the designated abnormal shadow candidate matches the clinical position information (body mark) of the examined position recorded in the ultrasonic image, determines that the abnormal shadow candidate and the ultrasonic image are suited for association or otherwise outputs the warning, thereby preventing the abnormal shadow candidate and the ultrasonic image, the clinical positions of which do not match, from being associated with each other and at the same time preventing the body mark information from being incorrectly registered in the server device 3.

When the abnormal shadow candidate is designated from the breast X-ray image displayed on the list display screen 432, the control unit 31 reads from the image DB 351 the abnormal shadow candidate and the ultrasonic image that is associated with the abnormal shadow candidate located at approximately the same position as the abnormal shadow candidate in the breast X-ray image of the same patient stored in the image DB 351, arranges the images side by side in time series, and causes the image display device 4 to display the images. As a result, the person performing the examination or the doctor can easily observe any change in the abnormal shadow candidate over time by looking at the ultrasonic image.

Note that what is described in the aforementioned embodiment is a preferred example of the present invention and is not to limit the present invention.

In the aforementioned embodiment, for example, the server device 3 and the image display device 4 separately configure a client server system, but the function of these two devices may instead be realized by a single device. That is, a storage unit of the device may store a program which causes a computer to function as a selection unit, a designation unit, a reception unit, a determination unit, an association unit, a monitoring unit, a storage unit, a generation unit, an extraction unit, a collation unit, a second designation unit, an abnormal shadow candidate extraction unit, and a display control unit, so that the functions are realized by the cooperation between a control unit of a CPU or the like and the program. The function of the abnormal shadow candidate detection device 2 may also be incorporated into the single device.

While the information of the abnormal shadow candidate detected from the abnormal shadow candidate detection device 2 is stored in the image DB 351 in association with the breast X-ray image from which the abnormal shadow candidate is detected in the aforementioned embodiment, the information of the abnormal shadow candidate input manually by the radiology technician with use of the input unit may be stored in association with that breast X-ray image as well. For example, the radiology technician in a radiology department may store in the image DB 351 the abnormal shadow candidate information of the abnormal shadow candidate, which is input (designated) by using the operation unit 42 from the breast X-ray image displayed on the viewer screen of the image display device 4, in association with the breast X-ray image from which the abnormal shadow candidate is detected, so that the abnormal shadow candidate information is displayed on the breast X-ray image to be designated according to an operation by the operation unit 42. Accordingly, the area determined to include the abnormal shadow candidate as a result of a person's observation can possibly be associated with the ultrasonic image.

While there has been described the example in the aforementioned embodiment where the subject site is the breast, the present invention may also be applied to a case where the ultrasound diagnosis on another site is to be aided.

While there has been disclosed the example in the aforementioned description where the hard disk and the semiconductor non-volatile memory are used as the computer-readable medium of the program according to the present invention, the present invention is not to be limited to such example. A portable recording medium such as a CD-ROM can be applied as another computer-readable medium. Moreover, a carrier wave is applied as a medium which provides program data according to the present invention through a communication line.

In addition, a detailed configuration and a detailed operation of each device configuring the medical image system can be modified as appropriate without departing from the gist of the present invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A medical image system comprising:
    a storage unit which stores a first medical image generated by a first imaging method in association with information on an abnormal shadow candidate in the first medical image;
    a selection unit which selects, from the first medical image stored in the storage unit, a medical image to be associated with a second medical image that is generated by a second imaging method different from the first imaging method;
    a designation unit which designates an abnormal shadow candidate from the first medical image selected;
    a reception unit which receives the second medical image newly created;

a determination unit which determines whether or not the first medical image selected is an image suited for association and whether or not the abnormal shadow candidate designated and the second medical image received satisfy a predetermined condition to be associated;

an association unit which stores in the storage unit the second medical image in association with the abnormal shadow candidate designated when the first medical image selected is determined to be the image suited for association as well as the abnormal shadow candidate designated and the second medical image received are determined to satisfy the predetermined condition; and a monitoring unit which monitors the association performed by the association unit, outputs a warning when there exists an abnormal shadow candidate that is not associated with the second medical image or the second medical image that is not associated with any of the abnormal shadow candidate of the first medical image, and stores in the storage unit the abnormal shadow candidate, which is not associated with the second medical image, in association with information indicating that there is no second medical image to be associated as well as the second medical image, with which none of the abnormal shadow candidate of the first medical image is associated, in association with information indicating that there is no abnormal shadow candidate to be associated.

2. The medical image system according to claim 1, wherein the determination unit determines that the image is suited for association when the first medical image selected is the latest among the first medical images formed by imaging the same subject site of the same patient and is imaged within a predetermined period.

3. The medical image system according to claim 1, further comprising:
 a generation unit which generates first clinical position information indicating a position of the abnormal shadow candidate when a subject site of the first medical image is viewed from the front, on the basis of the first medical image being selected;
 an extraction unit which extracts, from the second medical image, second clinical position information recorded in the second medical image and indicating an imaging position of the medical image when the subject site is viewed from the front; and
 a collation unit which collates the first clinical position information with the second clinical position information, wherein the determination unit determines that the predetermined condition is satisfied when a result of the collation performed by the collation unit indicates that the first clinical position information matches the second clinical position information.

4. The medical image system according to claim 1, further comprising a detection unit which detects the abnormal shadow candidate from the first medical image, wherein the storage unit stores the first medical image in association with information on the abnormal shadow candidate that is detected from the first medical image by the detection unit.

5. The medical image system according to claim 1, further comprising an input unit which inputs an area corresponding to the abnormal shadow candidate in the first medical image, wherein the storage unit stores the first medical image in association with information on the abnormal shadow candidate that is input by the input unit.

6. The medical image system according to claim 1, further comprising:
 a second designation unit which designates an abnormal shadow candidate from the first medical image selected;
 an abnormal shadow candidate extraction unit which reads from the storage unit the first medical image obtained by imaging the same subject site of the same patient as that in the first medical image including the abnormal shadow candidate designated by the second designation unit and extracts, from each first medical image being read, an abnormal shadow candidate that is located at about the same position as the abnormal shadow candidate designated by the second designation unit; and
 a display control unit which reads from the storage unit the second medical image stored in association with the abnormal shadow candidate extracted by the abnormal shadow candidate extraction unit, and arranges the second medical image being read in time series to be displayed on a display unit.

7. The medical image system according to claim 1, wherein the first medical image is a breast X-ray image, and the second medical image is an ultrasonic image of a mammary gland.

8. A non-transitory recording medium storing a computer readable program which causes a computer to function as:
 a selection unit which selects, from a storage unit which stores a first medical image generated by a first imaging method in association with information on an abnormal shadow candidate in the first medical image, a medical image to be associated with a second medical image that is generated by a second imaging method different from the first imaging method;
 a designation unit which designates an abnormal shadow candidate from the first medical image selected;
 a reception unit which receives the second medical image newly created;
 a determination unit which determines whether or not the first medical image selected is an image suited for association and whether or not the abnormal shadow candidate designated and the second medical image received satisfy a predetermined condition to be associated;
 an association unit which stores in the storage unit the second medical image in association with the abnormal shadow candidate designated when the first medical image selected is determined to be the image suited for association as well as the abnormal shadow candidate designated and the second medical image received are determined to satisfy the predetermined condition; and
 a monitoring unit which monitors the association performed by the association unit, outputs a warning when there exists an abnormal shadow candidate that is not associated with the second medical image or the second medical image that is not associated with any of the abnormal shadow candidate of the first medical image, and stores in the storage unit the abnormal shadow candidate, which is not associated with the second medical image, in association with information indicating that there is no second medical image to be associated as well as the second medical image, with which none of the abnormal shadow candidate of the first medical image is associated, in association with information indicating that there is no abnormal shadow candidate to be associated.

\* \* \* \* \*